(12) United States Patent
Im

(10) Patent No.: US 11,559,222 B2
(45) Date of Patent: Jan. 24, 2023

(54) RESPIRATORY SENSING DEVICE AND RESPIRATORY MONITORING SYSTEM INCLUDING THE SAME

(71) Applicants: MPROS, Jeonju-si (KR); INDUSTRIAL COOPERATION FOUNDATION CHONBUK NATIONAL UNIVERSITY, Jeonju-si (KR)

(72) Inventor: Jae Joong Im, Jeonju-si (KR)

(73) Assignee: MPROS, Jeonju-si (KR)

( * ) Notice: Subject to any disclaimer, the term of this patent is extended or adjusted under 35 U.S.C. 154(b) by 696 days.

(21) Appl. No.: 16/330,597

(22) PCT Filed: Nov. 8, 2018

(86) PCT No.: PCT/KR2018/013565
§ 371 (c)(1),
(2) Date: Mar. 5, 2019

(87) PCT Pub. No.: WO2019/093796
PCT Pub. Date: May 16, 2019

(65) Prior Publication Data
US 2021/0378545 A1    Dec. 9, 2021

Related U.S. Application Data

(60) Provisional application No. 62/583,465, filed on Nov. 8, 2017.

(30) Foreign Application Priority Data

Nov. 8, 2017  (KR) .................... 10-2017-0148341
Nov. 8, 2017  (KR) .................... 10-2017-0148342
Nov. 7, 2018  (KR) .................... 10-2018-0135594

(51) Int. Cl.
*A61B 5/08*     (2006.01)
*A61B 5/259*    (2021.01)
(Continued)

(52) U.S. Cl.
CPC ............ *A61B 5/0816* (2013.01); *A61B 5/002* (2013.01); *A61B 5/02208* (2013.01);
(Continued)

(58) Field of Classification Search
CPC ....... A61B 5/0816; A61B 5/259; A61B 5/002; A61B 5/02208; A61B 5/0826;
(Continued)

(56) References Cited

U.S. PATENT DOCUMENTS

2016/0287166 A1 * 10/2016 Tran ................. A61B 5/165

FOREIGN PATENT DOCUMENTS

EP    3449814 A1    3/2019
JP    2006-234720 A    7/2006
(Continued)

OTHER PUBLICATIONS

International Search Report for application No. PCT/KR2018/013564 dated Mar. 29, 2019.
KR Notice of Allowance in application No. 10-2017-0148342 dated Jun. 3, 2019.

*Primary Examiner* — Carl H Layno
*Assistant Examiner* — Aya Ziad Bakkar
(74) *Attorney, Agent, or Firm* — Maschoff Brennan

(57) ABSTRACT

The present invention relates to a respiratory sensing device attached to a patient's body and configured to acquire information regarding the patient's respiratory condition by sensing a vibration generated due to the patient's respiration using the piezoelectric effect and a respiratory monitoring system configured to output the acquired information regarding the patient's respiratory state.

15 Claims, 26 Drawing Sheets

(51) Int. Cl.
  *A61B 5/145* (2006.01)
  *A61B 5/00* (2006.01)
  *A61B 5/022* (2006.01)

(52) U.S. Cl.
  CPC ........ *A61B 5/0826* (2013.01); *A61B 5/14542* (2013.01); *A61B 5/259* (2021.01); *A61B 5/6824* (2013.01); *A61B 5/6826* (2013.01)

(58) Field of Classification Search
  CPC . A61B 5/14542; A61B 5/6824; A61B 5/6826; A61B 2560/0412; A61B 5/0205; A61B 7/04; A61B 5/6833; A61B 5/08; A61B 5/113; A61B 5/4818; A61B 5/024; A61B 2562/0204; A61B 2562/0247; A61B 5/282; A61B 5/4809; A61B 5/4815
  See application file for complete search history.

(56) References Cited

FOREIGN PATENT DOCUMENTS

| | | | |
|---|---|---|---|
| JP | 2013031568 A | * | 2/2013 |
| JP | 2015-080624 A | | 4/2015 |
| KR | 10-1327229 B1 | | 2/2012 |
| KR | 10-2015-0033197 A | | 4/2015 |
| KR | 10-2015-0076751 A | | 7/2015 |
| KR | 10-2016-0024887 A | | 3/2016 |
| KR | 10-2016-0127912 A | | 11/2016 |
| KR | 10-2016-0136758 A | | 11/2016 |
| KR | 10-1776237 B1 | | 11/2016 |
| KR | 20160136758 A | * | 11/2016 |
| WO | 2017-174031 A1 | | 10/2017 |

\* cited by examiner

RESPIRATORY SENSING DEVICE AND RESPIRATORY MONITORING SYSTEM INCLUDING THE SAME

TECHNICAL FIELD

The present invention relates to a respiratory sensing device and a respiratory monitoring system including the same, and more particularly, to a respiratory sensing device that senses a patient's respiration using a piezoelectric material and a respiratory monitoring system including the same.

BACKGROUND ART

Recently, efforts are being made to implement effective treatment by relaxing patients and minimizing their anxieties and fears through sedation. The sedation may include oral sedation, inhalation sedation, intravenous sedation, and the like depending on the provision method and may be generally classified into conscious sedation, deep sedation, and the like depending on the depth of sedation. However, when a patient's suppressed consciousness is induced by the sedation, the patient's physical abilities, such as an ability to secure an airway (trachea), may be significantly reduced because the patient may not be aware of clinical stimuli or may only respond to clinical stimuli minimally. Therefore, aggressive patient monitoring is necessary for safe sedation. In particular, monitoring a patient's respiratory state is very important because it is directly related to a surgical success rate and the patient's life.

An example method of monitoring respiratory depression to solve this problem may be a pulse oximetry using oxygen saturation, a ventilatory monitoring method using carbon dioxide partial pressure or tracheal auscultation, a circulatory monitoring method using blood pressure or electrocardiogram, or the like.

However, conventional respiratory monitoring methods have problems in that an apparatus for performing the methods has a complicated mechanical structure, is difficult to operate, is easily affected by ambient noise, is expensive, and the like. Accordingly, there is a need for a new type of respiratory monitoring apparatus that has a high signal-to-noise ratio (SNR) and is simple in structure and usage.

DETAILED DESCRIPTION OF THE INVENTION

Technical Problem

An object of the present invention is to provide a respiratory monitoring system that minimizes interference from electrical bio-signals generated from a patient's body, such as electrocardiogram (ECG) or electromyography (EMG).

An object of the present invention is to provide a respiratory sensing device and a respiratory monitoring system having a structure in which an electrode of a piezoelectric film can be easily grounded.

An object of the present invention is to provide a respiratory sensing device and a respiratory monitoring system in which a vibration transmission path from a patient's body to a piezoelectric film is easily formed without a strap member or an acoustic coupler for bringing the piezoelectric film into contact with the patient's body.

An object of the present invention is to provide a respiratory sensing device and a respiratory monitoring system that minimize the effect of an external vibration or the like generated due to a patient's tossing and turning and other factors besides respiration.

An object of the present invention is to provide a respiratory monitoring system having a disposable respiratory sensing device using a controller installed in an interface device.

An object of the present invention is to provide a respiratory monitoring system that outputs whether a patient's airway is secured, a sleep apnea state, and a patient snoring state.

Technical problems intended to be solved by the invention are not limited to the aforementioned objects, and other technical objects that are not described herein will be clearly understood by those skilled in the art from the following description and the accompanying drawings.

Technical Solution

According to an embodiment, there may be provided a respiratory sensing device attached to a patient's body and configured to sense a vibration generated due to the patient's respiration using a piezoelectric effect to acquire information regarding a respiratory state of the patient, the respiratory sensing device including a piezoelectric film including a thin film-shaped piezoelectric material, an upper electrode placed over the piezoelectric material, and a lower electrode placed under the piezoelectric material, wherein the piezoelectric material is interposed between the upper electrode and the lower electrode, and the piezoelectric film is configured to generate an electrical signal in the upper electrode and the lower electrode according to the vibration generated due to the patient's respiration; an adhesive layer placed under the piezoelectric film to face the lower electrode, provided as an adhesive material and thereby attached to the patient's body, and configured to transfer the vibration generated due to the patient's respiration to the piezoelectric film, the adhesive layer having an upper surface and a lower surface electrically connected to each other due to conductivity; and an insulating film interposed between the piezoelectric film and the adhesive layer and configured to block an electrical connection between the piezoelectric film and the adhesive layer, wherein a through-hole is formed in the insulating film to electrically connect the lower electrode and the adhesive layer to ground the lower electrode to the patient's body through the adhesive layer in order to decrease noise of the electrical signal due to the piezoelectric effect.

According to another embodiment, there may be provided a respiratory monitoring system including a respiratory sensing device attached to a patient's body and configured to output information regarding the patient's respiratory state acquired by sensing a vibration generated due to the patient's respiration using a piezoelectric effect, the respiratory sensing device including a piezoelectric film including a thin film-shaped piezoelectric material, an upper electrode placed over the piezoelectric material, and a lower electrode placed under the piezoelectric material, wherein the upper electrode and the lower electrode face each other with the piezoelectric material interposed therebetween, and the piezoelectric film is configured to generate an electrical signal in the upper electrode and the lower electrode according to the vibration generated due to the patient's respiration; an adhesive layer placed under the piezoelectric film to face the lower electrode, provided as an adhesive material and thus attached to the patient's body, and configured to transfer the vibration generated due to the patient's respiration to the piezoelectric film, the adhesive layer having an upper surface and a lower surface electrically connected to each other due to conductivity; and an insulating film interposed between the piezoelectric film and the adhesive layer and configured to block an electrical connection between the piezoelectric film and the adhesive layer, wherein a through-hole is formed in the insulating film to electrically connect the lower electrode and the adhesive layer to ground the lower electrode to the patient's body through the adhesive layer in order to decrease noise of the electrical signal due to the piezoelectric effect; and a respiratory monitoring device configured to receive the electrical signal from the respiratory sensing device and output the information regarding the patient's respiratory state on the basis of the electrical signal.

According to still another embodiment, there may be provided a respiratory sensing device attached to a patient's body and configured to sense a vibration generated due to the patient's respiration using a piezoelectric effect to acquire information regarding a respiratory state of the patient, the respiratory sensing device including a piezoelectric film including a thin film-shaped piezoelectric material, an upper electrode placed over the piezoelectric material, and a lower electrode placed under the piezoelectric material wherein the piezoelectric material is interposed between the upper electrode and the lower electrode and further including a sensing region for generating an electrical signal according to the vibration due to the respiration by overlapping and stacking the upper electrode, the piezoelectric material, and the lower electrode in the same region when viewed from a direction perpendicular to the thin film, wherein each of the upper electrode and the lower electrode has an opposing part placed in the sensing region and a terminal part extending to protrude outward from the opposing part in order to transmit the electrical signal to the outside; an adhesive layer placed under the piezoelectric film to face the lower electrode, provided as an adhesive material and thus attached to the patient's body, and configured to transfer the vibration generated due to the patient's respiration to the piezoelectric film, the adhesive layer having an upper surface and a lower surface electrically connected to each other due to conductivity; and an insulating film interposed between the piezoelectric film and the adhesive layer and configured to block an electrical connection between the piezoelectric film and the adhesive layer, the insulating film having a through-hole for electrically connecting the lower electrode and the adhesive layer in one region; a signal processing module including a connection terminal connected to the terminal part to receive the electrical signal, a circuit board configured to process the electrical signal, and a housing accommodating the connection terminal and the circuit board therein, wherein the signal processing module is placed close to the piezoelectric film to perform effective impedance matching and placed horizontally and parallel to the piezoelectric film such that the signal processing module does not overlap the piezoelectric film when viewed from the direction perpendicular to the thin film in order to decrease noise; a case configured to cover the insulating film while the signal processing module and the piezoelectric film are interposed therebetween to form an external appearance of the respiratory sensing device and configured to insulate the upper electrode and the signal processing module; and a cover attached to the lower surface of the adhesive layer and configured to protect the adhesive material.

According to still another embodiment, there may be provided a respiratory monitoring system configured to output information regarding a patient's respiratory state acquired by sensing a vibration generated due to the patient's respiration using a piezoelectric effect, the respiratory monitoring system including a respiratory sensing device including a piezoelectric film including a thin film-shaped piezoelectric material, an upper electrode placed over the piezoelectric material, and a lower electrode placed under the piezoelectric material wherein the piezoelectric material is interposed between the upper electrode and the lower electrode and further including a sensing region for generating an electrical signal according to the vibration due to the respiration by overlapping and stacking the upper electrode, the piezoelectric material, and the lower electrode in the same region when viewed from a direction perpendicular to the thin film, wherein each of the upper electrode and the lower electrode has an opposing part placed in the sensing region and a terminal part extending to protrude outward from the opposing part in order to transmit the electrical signal to the outside; an adhesive layer placed under the piezoelectric film to face the lower electrode, provided as an adhesive material and thus attached to the patient's body, and configured to transfer the vibration generated due to the patient's respiration to the piezoelectric film, the adhesive layer having an upper surface and a lower surface electrically connected to each other due to conductivity; and an insulating film interposed between the piezoelectric film and the adhesive layer and configured to block an electrical connection between the piezoelectric film and the adhesive layer, the insulating film having a through-hole for electrically connecting the lower electrode and the adhesive layer in one region; a signal processing module including a connection terminal connected to the terminal part to receive the electrical signal, a circuit board configured to process the electrical signal, and a housing accommodating the connection terminal and the circuit board therein, wherein the signal processing module is placed close to the piezoelectric film to perform effective impedance matching and placed horizontally and parallel to the piezoelectric film such that the signal processing module does not overlap the piezoelectric film when viewed from the direction perpendicular to the thin film in order to decrease noise; a case configured to cover the insulating film while the signal processing module and the piezoelectric film are interposed therebetween to form an external appearance of the respiratory sensing device and configured to insulate the upper electrode and the signal processing module; a cover attached to the lower surface of the adhesive layer and configured to protect the adhesive material; and a respiratory monitoring device configured to receive the electrical signal from the respiratory sensing device and output the information regarding the patient's respiratory state on the basis of the electrical signal.

According to still another embodiment, there may be provided a respiratory monitoring system configured to output information regarding a patient's respiratory state acquired by sensing a vibration generated due to the patient's respiration using a piezoelectric effect, the respiratory monitoring system including a disposable respiratory sensing device including a piezoelectric film including a thin film-shaped piezoelectric material, an upper electrode placed over the piezoelectric material, and a lower electrode placed under the piezoelectric material wherein the piezoelectric material is interposed between the upper electrode and the lower electrode, wherein the piezoelectric film generates a piezoelectric signal in the upper electrode and the lower electrode according to the vibration generated due to the patient's respiration and an insulating film placed under the lower electrode and configured to block an electrical connection from the piezoelectric film; and an interface device including a battery, a first power cable for supplying power to the disposable respiratory sensing device from the battery, a first communication cable for receiving the piezoelectric signal from the disposable respiratory sensing device, a controller configured to process the piezoelectric signal received through the first communication cable to generate a respiratory signal, and a communication module configured to transmit the respiratory signal to an external device.

Technical solutions intended to be solved by the invention are not limited to the aforementioned solutions, and other solutions that are not described herein will be clearly understood by those skilled in the art from the following description and the accompanying drawings.

Advantageous Effects of the Invention

According to an embodiment, by providing an insulating film between a piezoelectric film and a patient's body, interference from electrical bio-signals generated from the patient's body to the piezoelectric film is minimized, and thus it is possible to remove noise from respiratory signals.

According to another embodiment, due to a through-hole of an insulating film electrically connecting a lower electrode of a piezoelectric film to a conductive adhesive layer, the lower electrode is grounded to a patient's body, and thus it is possible to remove noise from respiratory signals.

According to still another embodiment, due to a piezoelectric film being provided as a gel-like material having flexibility and thus being connected to a patient's body through an adhesive layer adhered to the patient's body part, it is possible to easily transfer a vibration generated from the patient's body part to the piezoelectric film.

According to still another embodiment, due to an adhesive layer provided as a gel-like material and functioning as a band-pass filter for a vibration generated from a patient's body part, it is possible to minimize noise.

According to still another embodiment, by placing a controller in an interface device, a separate controller does not need to be used in a disposable respiratory sensing device, and thus it is possible to save costs.

According to still another embodiment, by measuring a patient's respiratory time interval and respiratory frequency, whether an trachea is closed and a sleep apnea state can be determined and output.

According to still another embodiment, by measuring the amplitude of a patient's respiratory signal, whether snoring is occurring or not may be determined and output.

Advantageous effects of the invention are not limited to the aforementioned effects, and other advantageous effects which are not mentioned here will be clearly understood by those skilled in the art from the following description and the accompanying drawings.

BEST MODE

Figure 1:
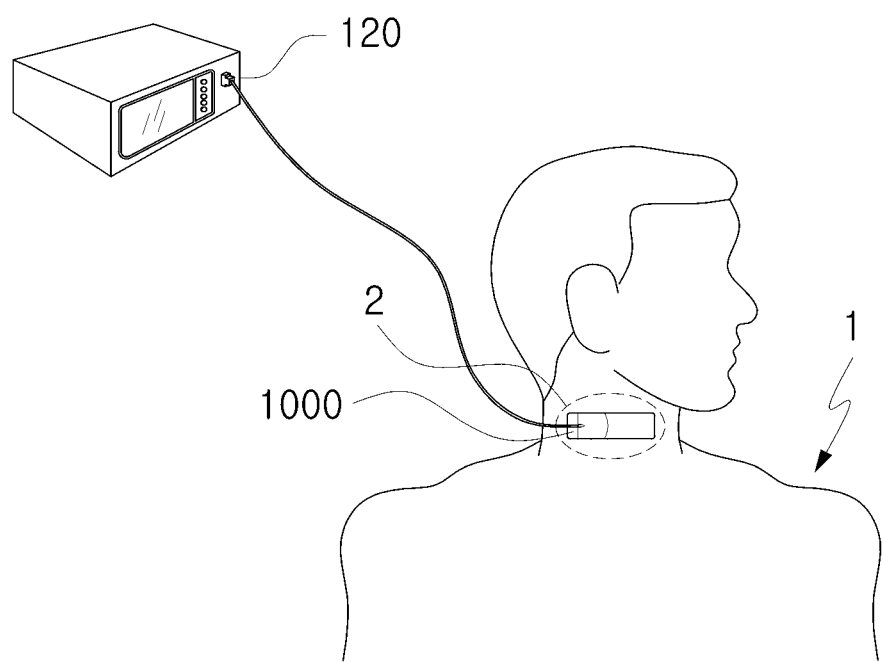
FIG. 1 is a schematic diagram of a respiratory monitoring system according to an embodiment of the present invention.

Hereinafter, embodiments of the present invention will be described in detail with reference to the accompanying drawings. However, the spirit of the present invention is not limited to the embodiments disclosed herein, and a person skilled in the art who understands the spirit of the present invention would be able to easily offer other embodiments within the scope of other retrograde invention or the present invention by adding, changing, and deleting components within the same spirit, and such embodiments are also intended to be included in the spirit of the present invention.

Also, the same reference numerals are used to designate elements having the same functions in the same range of spirit shown in the drawings of each embodiment.

In addition details of the generally known function and structure which may make the subject matter of the present invention unclear will be omitted.

According to an embodiment, there may be provided a respiratory sensing device attached to a patient's body and configured to sense a vibration generated due to the patient's respiration using a piezoelectric effect to acquire information regarding a respiratory state of the patient, the respiratory sensing device including a piezoelectric film including a thin film-shaped piezoelectric material, an upper electrode placed over the piezoelectric material, and a lower electrode placed under the piezoelectric material, wherein the piezoelectric material is interposed between the upper electrode and the lower electrode, and the piezoelectric film is configured to generate an electrical signal in the upper electrode and the lower electrode according to the vibration generated due to the patient's respiration; an adhesive layer placed under the piezoelectric film to face the lower electrode, provided as an adhesive material and thus attached to the patient's body, and configured to transfer the vibration generated due to the patient's respiration to the piezoelectric film, the adhesive layer having an upper surface and a lower surface electrically connected to each other due to conductivity; and an insulating film interposed between the piezoelectric film and the adhesive layer and configured to block an electrical connection between the piezoelectric film and the adhesive layer, wherein a through-hole is formed in the insulating film to electrically connect the lower electrode and the adhesive layer to ground the lower electrode to the patient's body through the adhesive layer in order to decrease noise of the electrical signal due to the piezoelectric effect.

Also, the respiratory sensing device may be provided with the through-hole which is an empty space extending to pass from an upper surface of the insulating film to a lower surface of the insulating film.

Also, the respiratory sensing device may be provided with the adhesive layer made of a hydrogel.

Also, the respiratory sensing device may be provided with the lower electrode grounded to the body by a portion of the hydrogel being inserted into the through-hole and brought into contact with a lower surface of the lower electrode.

Also, the piezoelectric film may include a sensing region for generating an electrical signal according to a vibration by overlapping and stacking the upper electrode, the piezoelectric material, and the lower electrode in the same region when viewed from a direction perpendicular to the piezoelectric film.

Also, the respiratory sensing device may be provided with each of the upper electrode and the lower electrode having an opposing part placed in the sensing region and a terminal part extending to protrude outward from the opposing part in order to transmit the electrical signal to the outside and with the through-hole formed at a position of the insulating film corresponding to the opposing part of the lower electrode.

According to another embodiment, there may be provided a respiratory monitoring system configured to output information regarding a patient's respiratory state acquired by sensing a vibration generated due to the patient's respiration using a piezoelectric effect, the respiratory monitoring system including a respiratory sensing device including a piezoelectric film including a thin film-shaped piezoelectric material, an upper electrode placed over the piezoelectric material, and a lower electrode placed under the piezoelectric material, wherein the upper electrode and the lower electrode face each other with the piezoelectric material interposed therebetween, and the piezoelectric film is configured to generate an electrical signal in the upper electrode and the lower electrode according to the vibration generated due to the patient's respiration; an adhesive layer placed under the piezoelectric film to face the lower electrode, provided as an adhesive material and thus attached to the patient's body, and configured to transfer the vibration generated due to the patient's respiration to the piezoelectric film, the adhesive layer having an upper surface and a lower surface electrically connected to each other due to conductivity; and an insulating film interposed between the piezoelectric film and the adhesive layer and configured to block an electrical connection between the piezoelectric film and the adhesive layer, wherein a through-hole is formed in the insulating film to electrically connect the lower electrode and the adhesive layer to ground the lower electrode to the patient's body through the adhesive layer in order to decrease noise of the electrical signal due to the piezoelectric effect; and a respiratory monitoring device configured to receive the electrical signal from the respiratory sensing device and output the information regarding the patient's respiratory state on the basis of the electrical signal.

According to still another embodiment, there may be provided a respiratory sensing device attached to a patient's body and configured to sense a vibration generated due to the patient's respiration using a piezoelectric effect to acquire information regarding a respiratory state of the patient, the respiratory sensing device including a piezoelectric film including a thin film-shaped piezoelectric material, an upper electrode placed over the piezoelectric material, and a lower electrode placed under the piezoelectric material wherein the piezoelectric material is interposed between the upper electrode and the lower electrode and further including a sensing region for generating an electrical signal according to the vibration due to the respiration by overlapping and stacking the upper electrode, the piezoelectric material, and the lower electrode in the same region when viewed from a direction perpendicular to the thin film, wherein each of the upper electrode and the lower electrode has an opposing part placed in the sensing region and a terminal part extending to protrude outward from the opposing part in order to transmit the electrical signal to the outside; an adhesive layer placed under the piezoelectric film to face the lower electrode, provided as an adhesive material and thus attached to the patient's body, and configured to transfer the vibration generated due to the patient's respiration to the piezoelectric film, the adhesive layer having an upper surface and a lower surface electrically connected to each other due to conductivity; and an insulating film interposed between the piezoelectric film and the adhesive layer and configured to block an electrical connection between the piezoelectric film and the adhesive layer, the insulating film having a through-hole for electrically connecting the lower electrode and the adhesive layer in one region; a signal processing module including a connection terminal connected to the terminal part to receive the electrical signal, a circuit board configured to process the electrical signal, and a housing accommodating the connection terminal and the circuit board therein, wherein the signal processing module is placed close to the piezoelectric film to perform effective impedance matching and placed horizontally and parallel to the piezoelectric film such that the signal processing module does not overlap the piezoelectric film when viewed from the direction perpendicular to the thin film in order to decrease noise; a case configured to cover the insulating film while the signal processing module and the piezoelectric film are interposed therebetween to form an external appearance of the respiratory sensing device and configured to insulate the upper electrode and the signal processing module; and a cover attached to the lower surface of the adhesive layer and configured to protect the adhesive material.

Also, the respiratory sensing device may be provided with the case further including an accommodation part having a space for housing the signal processing module therein and wherein the adhesive layer further extends a predetermined length away from the piezoelectric film from a region corresponding to the accommodation part in order to provide sufficient adhesion.

Also, the respiratory sensing device may be provided with the signal processing module further including a cable connected to the circuit board in order to transmit the electrical signal processed by the circuit board to the outside, wherein the connection terminal is connected to the terminal part at one side of the signal processing module, wherein the cable is connected to the circuit board horizontally on another side of the signal processing module, the one end is facing toward the piezoelectric film and the other end is facing away from the piezoelectric film in order to reduce influence of the cable on the piezoelectric film.

Also, the respiratory sensing device may be provided with the insulating film, the adhesive layer, and the case aligned and stacked such that any one layer does not protrude to the outside when the insulating film, the adhesive layer, and the case are piled up.

Also, the respiratory sensing device may be provided with the piezoelectric film including at least one material selected from among a polyvinylidene fluoride (PVDF) film, lead zirconate titanate (PZT), and quartz.

According to still another embodiment, there may be provided a respiratory monitoring system configured to output information regarding a patient's respiratory state acquired by sensing a vibration generated due to the patient's respiration using a piezoelectric effect, the respiratory monitoring system including a respiratory sensing device including a piezoelectric film including a thin film-shaped piezoelectric material, an upper electrode placed over the piezoelectric material, and a lower electrode placed under the piezoelectric material wherein the piezoelectric material is interposed between the upper electrode and the lower electrode and further including a sensing region for generating an electrical signal according to the vibration due to the respiration by overlapping and stacking the upper electrode, the piezoelectric material, and the lower electrode in the same region when viewed from a direction perpendicular to the thin film, wherein each of the upper electrode and the lower electrode has an opposing part placed in the sensing region and a terminal part extending to protrude outward from the opposing part in order to transmit the electrical signal to the outside; an adhesive layer placed under the piezoelectric film to face the lower electrode, provided as an adhesive material and thus attached to the patient's body, and configured to transfer the vibration generated due to the patient's respiration to the piezoelectric film, the adhesive layer having an upper surface and a lower surface electrically connected to each other due to conductivity; and an insulating film interposed between the piezoelectric film and the adhesive layer and configured to block an electrical connection between the piezoelectric film and the adhesive layer, the insulating film having a through-hole for electrically connecting the lower electrode and the adhesive layer in one region; a signal processing module including a connection terminal connected to the terminal part to receive the electrical signal, a circuit board configured to process the electrical signal, and a housing accommodating the connection terminal and the circuit board therein, wherein the signal processing module is placed close to the piezoelectric film to perform effective impedance matching and placed horizontally and parallel to the piezoelectric film such that the signal processing module does not overlap the piezoelectric film when viewed from the direction perpendicular to the thin film in order to decrease noise; a case configured to cover the insulating film while the signal processing module and the piezoelectric film are interposed therebetween to form an external appearance of the respiratory sensing device and configured to insulate the upper electrode and the signal processing module; a cover attached to the lower surface of the adhesive layer and configured to protect the adhesive material; and a respiratory monitoring device configured to receive the electrical signal from the respiratory sensing device and output the information regarding the patient's respiratory state on the basis of the electrical signal.

According to still another embodiment, there may be provided a respiratory monitoring system configured to display information regarding a patient's respiratory state acquired by sensing a vibration generated due to the patient's respiration using a piezoelectric effect, the respiratory monitoring system including a disposable respiratory sensing device including a piezoelectric film including a thin film-shaped piezoelectric material, an upper electrode placed over the piezoelectric material, and a lower electrode placed under the piezoelectric material wherein the piezoelectric material is interposed between the upper electrode and the lower electrode, wherein the piezoelectric film generates a piezoelectric signal in the upper electrode and the lower electrode according to the vibration generated due to the patient's respiration and an insulating film placed under the lower electrode and configured to block an electrical connection from the piezoelectric film; and an interface device including a battery, a first power cable for supplying power to the disposable respiratory sensing device from the battery, a first communication cable for receiving the piezoelectric signal from the disposable respiratory sensing device, a controller configured to process the piezoelectric signal received through the first communication cable to generate a respiratory signal, and a communication module configured to transmit the respiratory signal to an external device.

Also, the respiratory monitoring system further including a respiratory monitoring device configured to receive the respiratory signal from the interface device and display the information regarding the patient's respiratory state on the basis of the respiratory signal may be provided.

Also, the respiratory monitoring system further including a pulse oximeter installed at one point of the patient's finger and configured to measure blood oxygen saturation may be provided, wherein the interface device includes a second communication cable having one end electrically connected to the controller and another end electrically connected to the pulse oximeter, the second communication cable being configured to receive a signal including information regarding the blood oxygen saturation from the pulse oximeter.

Also, the respiratory monitoring system may be provided with the interface device including a second power cable for supplying power from the battery to the pulse oximeter.

Also, the respiratory monitoring system may be provided with the interface device generating the respiratory signal in further consideration of the information regarding the oxygen saturation.

Also, the respiratory monitoring system further including an upper arm blood pressure monitor installed on the patient's upper arm and configured to measure blood pressure of the patient's upper arm may be provided, wherein the interface device is electrically connected to the upper arm blood pressure monitor and configured to receive a signal including the information regarding the blood pressure of the upper arm.

Also, the respiratory monitoring system may be provided with the interface device installed in the upper arm blood pressure monitor.

Also, the respiratory monitoring system further including a wrist blood pressure monitor configured to sense Korotkoff sounds from the patient's wrist, measure blood pressure corresponding to a wrist blood pressure value, and correct blood pressure corresponding to the wrist blood pressure value using a signal reflecting an upper arm blood pressure value may be provided, wherein the interface device is electrically connected to the wrist blood pressure monitor and configured to receive the signal reflecting the upper arm blood pressure value.

Also, the respiratory monitoring system may be provided with the communication module being a wireless communication module using at least one of Bluetooth, Zigbee, and Wi-Fi.

Also, the respiratory monitoring system may be provided with the interface device determining that the patient's airway (trachea) is not secured when the piezoelectric signal corresponds to a first predetermined condition and determines that the patient is in a sleep apnea state when the piezoelectric signal corresponds to a second predetermined condition and then transmits the respiratory signal, wherein the first predetermined condition is that a time interval at which the piezoelectric signal is sensed by the interface device exceeds a first predetermined time interval or that the number of times the piezoelectric signal is sensed by the interface device per reference time is less than a first predetermined number, the second predetermined condition is that a time interval at which the piezoelectric signal is sensed by the interface device exceeds a second predetermined time interval or that the number of times the piezoelectric signal is sensed by the interface device per reference time is less than a second predetermined number, the second predetermined time interval is greater than the first predetermined time interval, and the second predetermined number is greater than the first predetermined number.

Also, the respiratory monitoring system may be provided with the interface device determining that the patient is in a snoring state when the piezoelectric signal corresponds to a third predetermined condition and then transmits the respiratory signal, and wherein the third predetermined condition is that the piezoelectric signal has an amplitude exceeding a predetermined value.

Also, the respiratory monitoring system may be provided with the respiratory sensing device including an adhesive layer which is placed under the piezoelectric film to face the lower electrode, which is provided as an adhesive material and thus attached to the patient's body, and which is configured to transfer the vibration generated due to the patient's respiration to the piezoelectric film, the adhesive layer having an upper surface and a lower surface electrically connected to each other due to conductivity, wherein the insulating film is configured to block an electrical connection between the piezoelectric film and the adhesive layer and has a through-hole formed to electrically connect the lower electrode and the adhesive layer to ground the lower electrode to the patient's body through the adhesive layer in order to decrease noise of the electrical signal due to the piezoelectric effect.

A respiratory monitoring system 100 according to an embodiment of the present invention will be described below.

The respiratory monitoring system 100 is a system that diagnoses a patient's respiratory state by measuring a vibration due to a patient's respiration through a respiratory sensing device 1000 attached to the patient's body part and analyzing the measured vibration.

Figure 15:
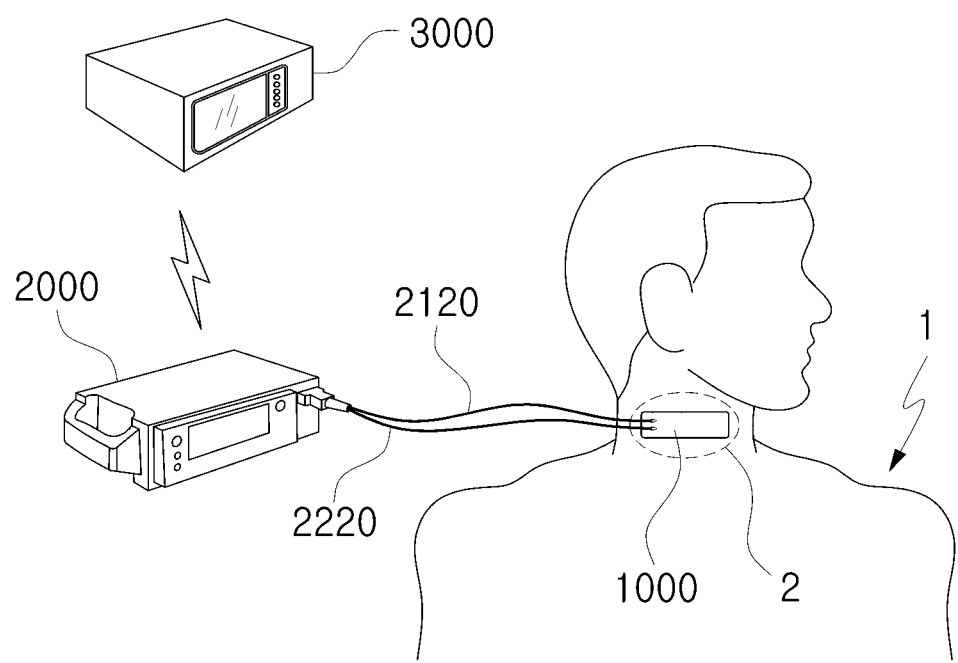
FIG. 15 is another schematic diagram of a respiratory monitoring system according to an embodiment of the present invention.

FIG. 1 is a schematic diagram of the respiratory monitoring system 100 according to an embodiment of the present invention, and FIG. 15 is another schematic diagram of the respiratory monitoring system 100 according to an embodiment of the present invention.

Referring to FIG. 1, the respiratory monitoring system 100 may include a respiratory sensing device 1000 and a respiratory monitoring device 3000.

The respiratory sensing device 1000 may be attached to a body part, such as an airway, of a patient 1 and may be configured to sense a vibration due to respiration of the patient 1.

An attachment site 2 to which the respiratory sensing device 1000 is attached may be a place where motion occurs while the patient respires regularly. For example, the attachment site 2 may be a thorax that reflects a change in volume of lungs and abdominal cavity, a wrist that allows a pulse to be sensed through a vein, a portion of the thorax under which a heart is placed, or a philtrum. Preferably, the respiratory sensing device 1000 may be attached to a neck, as shown in FIG. 1. More preferably, the respiratory sensing device 1000 may be attached to a portion of the neck corresponding to an airway having relatively large movement due to respiration of the patient 1. It will be appreciated that the attachment site for the respiratory sensing device 1000 is not limited to the above example.

The respiratory sensing device 1000 may generate electrical signals according to the piezoelectric effect when a vibration is generated due to respiration. The respiratory sensing device 1000 may transmit the electrical signals to the respiratory monitoring device 3000. Here, the respiratory sensing device 1000 may process the signals generated according to the piezoelectric effect and transmit the processed signals.

A detailed description of the respiratory sensing device 1000 will be described later.

The respiratory monitoring device 3000 may output information regarding the respiratory state of the patient 1 to a user in real time or under certain conditions. As an example, the respiratory monitoring device 3000 may have audiovisual information output means, such as a display or a speaker, and thus may visually display respiratory signals through the display or may audibly provide respiratory state-associated information to the user through the speaker.

Also, the respiratory monitoring device 3000 may sense occurrence of an abnormality in the health condition of the patient 1 through the respiratory state of the patient 1 and then output an alarm related thereto. As an example, when a abnormal respiratory state or an apnea state is maintained, the respiratory monitoring device 3000 may provide an alarm to the user through the display, the speaker, or the like.

The respiratory monitoring device 3000 may be an information computing apparatus for performing the above-described functions. The respiratory monitoring device 3000 may be implemented as a computer or the like as hardware, software, or a combination thereof. The respiratory monitoring device 3000 may be an information processing apparatus for storing and processing data in hardware and may be provided in the form of a program or codes for driving a circuit in software.

The respiratory monitoring device 3000 may be wired or wirelessly connected to one or more respiratory sensing devices 1000 or other sensing devices. For example, the respiratory sensing devices 1000 may be attached to different body parts of the same patient 1, and also another external device may be a mechanism for measuring oxygen saturation (a pulse oximeter). The respiratory sensing device 1000 may independently process or correlate information received from another respiratory sensing device 1000 or an external device to perform relevant operations.

Referring to FIG. 15, a respiratory monitoring system 100 may include a respiratory sensing device 1000, an interface device 2000, and a monitoring device 3000.

The respiratory sensing device 1000 may generate piezoelectric signals, which are electrical signals, according to the piezoelectric effect when a vibration is generated due to respiration. The respiratory sensing device 1000 may transmit the electrical signals to the interface device 2000. The interface device 2000 may process the signals generated according to the piezoelectric effect to generate respiratory signals. In this case, the interface device 2000 may transmit the respiratory signals to the monitoring device 3000.

The interface device 2000 may receive piezoelectric signals, which are electrical signals, from the respiratory sensing device 1000 and process the piezoelectric signals to generate respiration signals. In this case, the interface device 2000 may transmit the respiratory signals to the monitoring device 3000 by means of a communication module.

The respiratory sensing device 1000 and the monitoring device 3000 have been described above. However, the monitoring device 3000 may receive the respiratory signals from the interface device 2000 and monitor a respiratory state of a patient 1 using the received respiratory signals.

Figure 16:
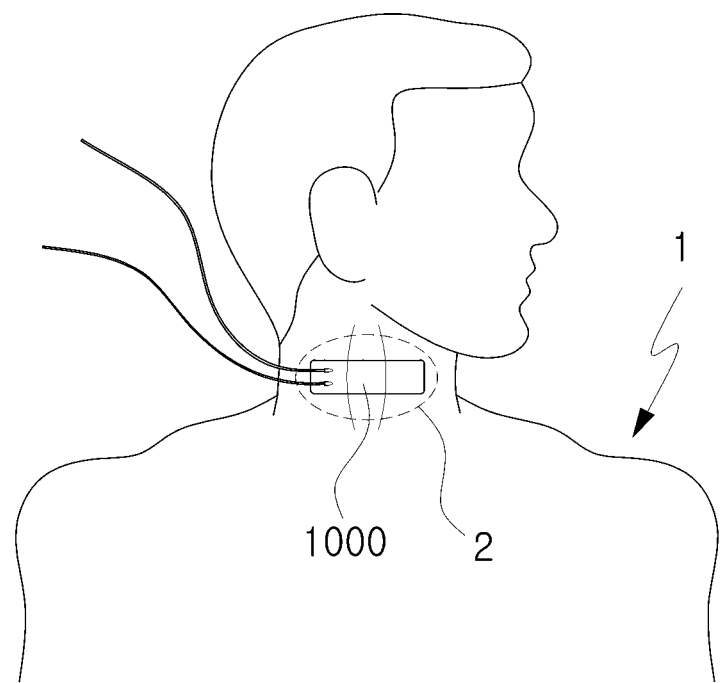
FIG. 16 is another diagram showing a usage state of a respiratory sensing device according to an embodiment of the present invention.
Figure 17:
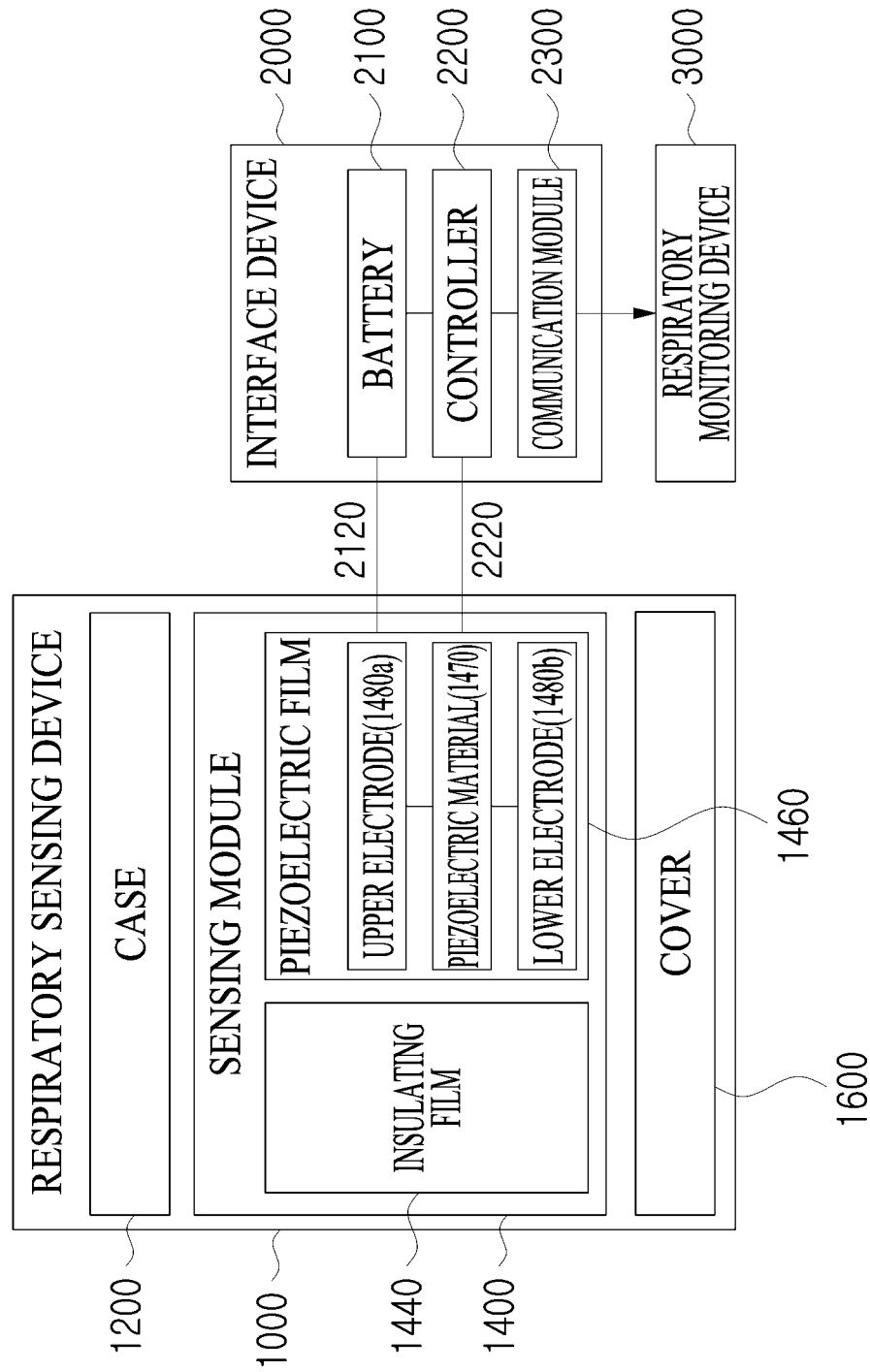
FIG. 17 is a block diagram showing a configuration of a respiratory monitoring system according to an embodiment of the present invention.

Also, the respiratory monitoring device 3000 may be wired or wirelessly (not shown) connected to one or more respiratory sensing devices 1000 or other sensing devices (see FIGS. 15 to 17). For example, the respiratory sensing devices 1000 may be attached to different body parts of the same patient 1, and also another external device may be a pulse oximeter that measures oxygen saturation. The respiratory monitoring device 3000 may independently process or correlate information received from the respiratory sensing device 1000 or other sensing devices to perform relevant operations.

The respiratory sensing device 1000 according to an embodiment of the present invention will be described in detail below.

Figure 2:
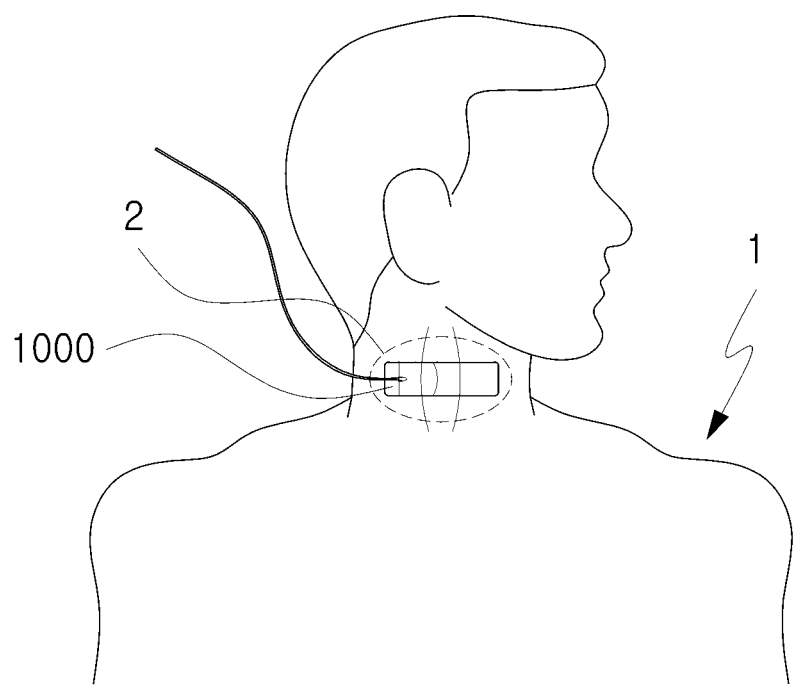
FIG. 2 is a diagram showing a usage state of a respiratory sensing device according to an embodiment of the present invention.

FIG. 2 is a diagram showing a usage state of the respiratory sensing device 1000 according to an embodiment of the present invention, and FIG. 16 is another diagram showing a usage state of the respiratory sensing device 1000 according to an embodiment of the present invention.

The respiratory sensing device 1000 may be attached to a body part of the patient 1 in which a vibration is generated due to respiration. The body part of the patient 1 to which the respiratory sensing device 1000 is attached is hereinafter referred to as an attachment site 2.

Referring to FIG. 2, the attachment site 2 may be a laryngeal prominence. The laryngeal prominence is a portion of a lower respiratory tract in which a fine vibration is generated due to inhalation and exhalation upon respiration. Accordingly, the respiratory sensing device 1000 may be attached to the laryngeal prominence to measure a vibration and movement generated upon respiration. In FIG. 2, it is shown that the attachment site 2 is a laryngeal prominence, but it is to be noted that the attachment site 2 in the present invention is not limited thereto.

The respiratory sensing device 1000 may have various shapes. For example, as shown in FIG. 2, the respiratory sensing device 1000 may have a generally rectangular shape.

The respiratory sensing device 1000 may be attached to most effectively measure a movement due to respiration in consideration of the shape of the laryngeal prominence. For example, the respiratory sensing device 1000 may be placed at the laryngeal prominence such that a longer side of the rectangle is horizontal. The respiratory sensing device 1000 may be attached such that the long side surrounds the laryngeal prominence. In this case, the laryngeal prominence may be placed at the center of the long side of the respiratory sensing device 1000 or may be placed in a portion biased toward one side of the respiratory sensing device 1000.

A cable for transmitting electrical signals generated by a vibration to the respiratory monitoring device 3000 may extend from one side of the respiratory sensing device 1000. In this case, in order not to generate noise, the cable may extend opposite to the laryngeal prominence without crossing the laryngeal prominence.

The cable will be described in detail with reference to FIG. 17.

The configurations of the respiratory sensing device 1000 and the respiratory monitoring system 100 according to an embodiment of the present disclosure will be described below.

Figure 3:
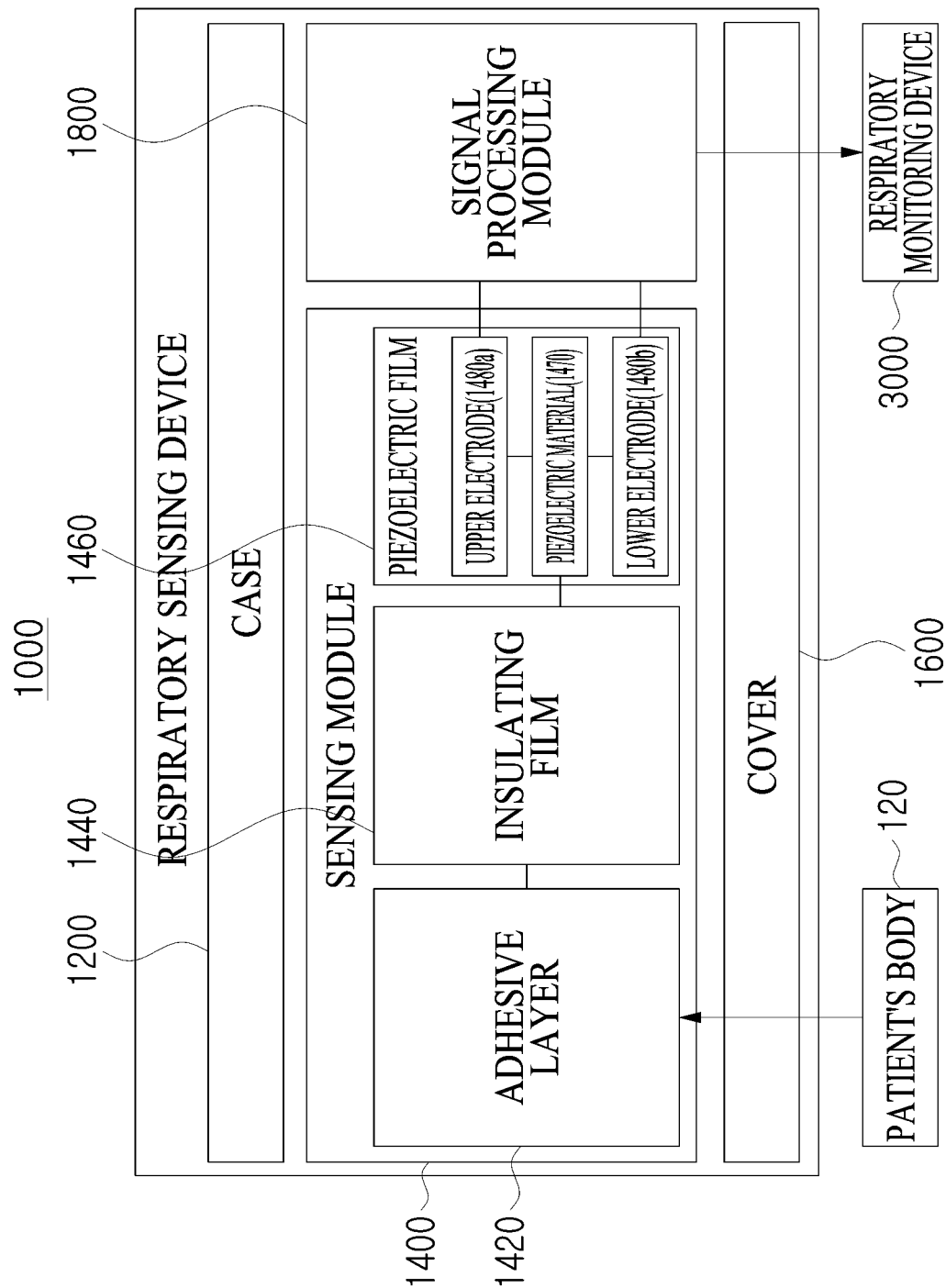
FIG. 3 is a block diagram showing a configuration of a respiratory sensing device according to an embodiment of the present invention.

FIG. 3 is a block diagram showing the configuration of the respiratory sensing device 1000 according to an embodiment of the present invention.

Referring to FIG. 3, the respiratory sensing device 1000 may include a case 1200, a sensing module 1400, a cover 1600, and a signal processing module 1800. In FIG. 3, it is shown that all of the above-described elements are formed integrally with the respiratory sensing device 1000, but it is also possible that the signal processing module 1800 is omitted from the respiratory sensing device 1000 and is separately placed on the outside.

The respiratory sensing device 1000 may have an external appearance formed by the case 1200. The respiratory sensing device 1000 may have the sensing module 1400 for sensing a vibration and the signal processing module 1800 for processing electric signals due to a vibration, which are placed therein or therebelow, and may include a cover 1600 that covers an adhesive material.

The case 1200 is an element for forming the external appearance of the respiratory sensing device 1000.

The case 1200 may protect the other elements of the respiratory sensing device 1000 against external impact, contamination, or the like. The case 1200 may provide a space where the respiratory sensing device 1000 is housed. For example, the case 1200 may be provided in a thin-film shape to cover the sensing module 1400 and the signal processing module 1800.

The case 1200 may be made of a flexible material so that the case 1200 may be changed in shape to match the shape of a body part to which the respiratory sensing device 1000 is attached. For example, the case 1200 may be made of a kind of rubber.

The case 1200 may be made of a non-conductor. The case 1200 may insulate the other elements in the respiratory sensing device 1000 so that electrical signals in the respiratory sensing device 1000 cannot be leaked to the outside except for the purpose of data transmission.

Also, the case 1200 may serve to prevent an external vibration, which is generated from a side opposite to the sensing module 1400 for sensing a vibration, from being transferred to the sensing module 1400. In an environment, such as a surgery room, where the respiratory sensing device 1200 is used, audio signals irrelevant to respiration may be generated due to a surgery or other causes. For example, the case 1200 may be made of a material such as rubber to reduce an external audio signal. Thus, by the external audio signal being blocked from being transferred to the sensing module 1400, it is possible to remove or reduce noise from the sensing module 1400.

Furthermore, the case 1200 may amplify a vibration due to respiration, which is sensed by the sensing module. The vibration due to respiration mainly has a frequency of 200 Hz to 1,000 Hz, and the case 1200 may be made of a material having a resonance frequency corresponding to the frequency band to amplify the vibration sensed by the sensing module 1400.

The sensing module 1400 may be an element for generating electrical signals according to the vibration of the attachment site 2. The sensing module 1400 may be adhered to the attachment site 2 and may generate electric signals using the piezoelectric effect when a vibration generated in the attachment site 2 is transferred to the inside.

The sensing module 1400 may include an adhesive layer 1420, an insulating film 1440, and a piezoelectric film 1460.

The adhesive layer 1420 may provide an adhesive force so that the respiratory sensing device 1000 can be attached to the attachment site 2. Also, the adhesive layer 1420 may be conductive and thus may function as an electrical path for grounding the piezoelectric film 1460 to a human body.

The insulating film 1440 may electrically insulate the piezoelectric film 1460 and the adhesive layer 1420 and thus may block or reduce external influences due to an electrocardiogram (ECG) signal and an electromyography (EMG) signal generated in the body of the patient 1.

The piezoelectric film 1460 may generate electrical signals in response to a vibration transferred through the adhesive layer 1420 and the insulating film 1440.

In detail, the adhesive layer 1420 may contain an adhesive material. The adhesive material may provide a contact force capable of bringing the respiratory sensing device 1000 into close contact with the surface of the attachment site 2 without gaps therebetween during vibration measurement and may provide a contact force such that the respiratory sensing device 1000 can be easily separated by an external force after vibration measurement. The adhesive material may be applied to the entirety of the adhesive layer 1420 or to only a portion of the adhesive layer 1420.

The adhesive layer 1420 may be made of a flexible material so that the adhesive layer 1420 can be flexibly changed in shape to match the curvature and shape of the surface of the attachment site 2. This may increase the surface area in which the adhesive layer 1420 is brought into contact with a human body. Thus, the adhesive force between the adhesive layer 1420 and the human body may increase. Also, the vibration transferred to the attachment site 2 may be effectively transferred to the adhesive layer 1420.

Also, the adhesive layer 1420 may function to transfer the vibration of the attachment site 2 to the piezoelectric film 1460 through the insulating film 1440. In this case, the vibration transferred by the adhesive layer 1420 to upper layers may be selective. For example, the adhesive layer 1420 may allow transmission of waves with the frequency of the vibration due to respiration and block waves with the other frequencies. That is, the adhesive layer 1420 may function as a kind of bandpass filter for the vibration transferred to the attachment site 2. Thus, the adhesive layer 1420 may enhance sensing sensitivity. This will be described in detail below.

The adhesive layer 1420 may be made of a material harmless to a human body. In particular, since some of the adhesive material may remain on the human body after separation from the human body, it may be important that the adhesive material is made of a material harmless to the human body.

Also, in detail, the insulating film 1440 may be made of an insulating material to insulate the piezoelectric film 1460. In particular, by preventing contact between the piezoelectric film 1460 and the adhesive layer 1420, the insulating film 1440 may insulate the piezoelectric film 1460. By the insulating film 1440 blocking electromagnetic waves radiated from the human body from reaching the piezoelectric film, it is possible to minimize influence of the electromagnetic waves. This will be described in more detail below.

Also, the insulating film 1440 may re-transfer the vibration transferred through the adhesive layer 1420 to the piezoelectric film 1460.

Also, the insulating film 1440 may be flexibly changed in shape to match the curvature of the attachment site 2. The change in shape may help re-transfer the vibration transferred from the adhesive layer 1420 to the piezoelectric film 1460.

In one region of the insulating film 1440, the piezoelectric film 1460 may be grounded to the human body through the adhesive layer 1420. Due to the piezoelectric film 1460 being grounded to the human body with a large electric capacity, it is possible to facilitate setting of a reference potential and decrease signal noise.

Also, in detail, the piezoelectric film 1460 may include an upper electrode 1480*a*, a piezoelectric material 1470, and a lower electrode 1480*b*. The upper electrode 1480*a*, the piezoelectric material 1470, and the lower electrode 1480*b* may be provided in the form of a thin film and may play a role similar to that of a capacitor by being piled up with their main surfaces facing each other. The piezoelectric material 1470 may generate a potential difference between the upper electrode 1480*a* and the lower electrode 1480*b* in response to an external force by the piezoelectric effect. Electrical signals may be generated by the potential difference between the upper electrode 1480*a* and the lower electrode 1480*b*.

The piezoelectric effect refers to a phenomenon in which a voltage is generated between two opposing surfaces of a piezoelectric crystal due to a pressure or a distortion force acting on the crystal. Alternatively, the piezoelectric effect refers to a reverse phenomenon in which a distortion varying at the frequency of a voltage applied between the two surfaces occurs. The nature of the piezoelectric effect is closely related to occurrence of an electric dipole moment in a solid. The reason for which polarization changes when a mechanical force is applied is that the direction of the dipole moment changes due to a change in molecular arrangement direction caused by an external stress. Examples of a material exhibiting the piezoelectric effect include quartz, berlinite, sucrose, topaz and tourmaline, which are present in nature, and further include ceramics having a perovskite structure such as gallium phosphide, langasite or PZT, and zinc oxide and ceramics having a tungsten bronze structure, all of which are artificial piezoelectric materials. From thereamong, polyvinylidene fluoride (PVDF), which is widely used and has a superior piezoelectric effect, can induce a piezoelectric effect several times larger than quartz.

The piezoelectric material 1470 may be a material selected from among the above-described piezoelectric materials.

The cover 1600 is an element for covering the adhesive layer 1420. The cover 1600 may maintain a high quality adhesive force by preventing the adhesive layer 1420 from being exposed to foreign substances before the respiratory sensing device 1000 is attached to the attachment site 2. The cover 1600 being removed immediately before the respiratory sensing device 1000 is attached to the attachment site 2 may expose the adhesive layer 1420 to the outside and allow the adhesive layer 1420 to be attached to skin. The cover 1600 may be adhered to the adhesive layer 1420 with a certain level of adhesive force so as to not be removed by a small external force. However, the cover 1600 should be adhered to the adhesive layer 1420 with a certain level of adhesive force or lower so as to be easily removed by a certain level of external force or higher. Also, the cover 1600 may be made of a material capable of withstanding a certain tensile force and shear force so as to not be damaged when being removed.

The signal processing module 1800 is an element for receiving and processing electric signals.

The signal processing module 1800 may receive an electric signal from the sensing module 1400.

The signal processing module 1800 may perform an operation necessary to process the received electric signal. For example, the signal processing module 1800 may perform a process for removing noise from the received electric signal and, to this end, may include a noise removal circuit.

Alternatively, the signal processing module 1800 may perform impedance matching on the output of the sensing module 1400 and, to this end, may include a field-effect transistor (FET) circuit.

Alternatively, the signal processing module 1800 may perform an operation for amplifying electric signals.

Subsequently, the signal processing module 1800 may transmit the processed electric signal to the respiratory monitoring device 3000 by cable.

FIG. 17 is a block diagram showing a configuration of a respiratory monitoring system 100 according to an embodiment of the present invention.

Referring to FIG. 17, a respiratory sensing device 1000 may include a case 1200, a sensing module 1400, and a cover 1600. Referring to FIG. 17, a respiratory sensing device 1000 may include a case 1200, a sensing module 1400, and a cover 1600. The case 1200, the sensing module 1400, and the cover 1600 have been described above.

An interface device 2000 may process a piezoelectric signal received from the sensing module 1400 to generate a respiratory signal.

In detail, the interface device 2000 may perform various kinds of algorithms for checking a respiratory state from an electrical signal or may perform various kinds of preprocessing operations in addition to removal of noise from the electrical signal to perform the algorithm. According to an analysis result acquired according to the above process, the interface device 120 may check a respiratory state of the patient 1 and generate a respiratory signal.

The piezoelectric signal, which is an electric signal received by the interface device 2000 from the respiratory sensing device 1000, may contain a component caused by various vibrations generated irrespective of respiration of a patient 1. The component may include a vibration generated by an endoscope and surgical instruments that unintentionally touch the airway of the patient 1. Alternatively, the noise may be a vibration generated when the patient 1 swallows his/her saliva. Alternatively, the noise may be a vibration generated when the patient 1 suddenly moves.

One example of the preprocessing operations of the interface device 2000 may include a noise filtering operation for removing the component caused by the vibration irrespective of the respiration from the electrical signal.

Information regarding the respiratory state acquired by the interface device 2000 may be features related to respiration, such as an apnea state, a snoring state, an exhalation flow rate, a tidal volume, and the like. Furthermore, the interface device 2000 may diagnose a health state of the patient 1. For example, among the respiratory characteristics, the interface device 2000 may diagnose abnormal signs or diseases such as apnea in which respiration is ceased for a certain time or longer, hypopnea in which respiration is reduced, or Upper Airway Resistance Syndrome (UARS).

Also, the interface device 2000 may sense occurrence of an abnormality in the health condition of the patient 1 through the respirator state of the patient 1 and may transmit an associated respiratory signal to the respiratory monitoring device 3000. As an example, when a abnormal respiratory state or an apnea state is maintained, the interface device 2000 may transmit a signal including information corresponding to the abnormal respiratory state or the apnea state to the respiratory monitoring device 3000.

In detail, when a time interval at which the piezoelectric signal is sensed by the interface device 2000 exceeds a first predetermined time interval or when the number of times the piezoelectric signal is sensed by the interface device 2000 per reference time is less than a first predetermined number, the interface device 2000 may determine that the airway of the patient 1 is not secured and may transmit a signal including associated information to the respiratory monitoring device 3000. In this case, the first predetermined time interval and the first predetermined number may change differently depending on the state of the patient 1 and the sedation applied to the patient 1.

Also, when a time interval at which the piezoelectric signal is sensed by the interface device 2000 exceeds a second predetermined time interval or when the number of times the piezoelectric signal is sensed by the interface device 2000 per reference time is less than a second predetermined number, the interface device 2000 may determine that the patient 1 is in the sleep apnea state and transmit a signal including associated information to the respiratory monitoring device 3000. In this case, the second predetermined time interval and the second predetermined number may change differently depending on the age, medical history, gender, and weight of the patient 1 and the sedation applied to the patient 1. It will be appreciated that various other conditions may be added in addition to the above listed conditions. However, the second predetermined time interval may be greater than the first predetermined time interval.

Also, when the piezoelectric signal corresponds to a third predetermined condition, the interface device 2000 may transmit a respiratory signal, which includes information indicating that the patient 1 is snoring, to the respiratory monitoring device 3000. In this case, the third predetermined condition indicates that the amplitude of the piezoelectric signal exceeds a predetermined value, and the predetermined value may be changed differently depending on at least one of the age, medical history, gender, and weight of the patient 1. It will be appreciated that various other conditions may be added in addition to the above listed conditions.

The interface device 2000 may be an information computing apparatus for performing the above-described functions. The interface device 2000 may be implemented as a computer or the like in hardware, software, or a combination thereof. The interface device 2000 may be an information processing apparatus for storing and processing data in hardware and may be provided in the form of a program or codes for driving a circuit in software.

The interface device 2000 may be wired or wirelessly connected to one or more respiratory sensing device 1000 or other sensing devices (not shown). For example, the respiratory sensing devices 1000 may be attached to different body parts of the same patient 1, and the other external apparatus may be a pulse oximeter 1700 for measuring oxygen saturation. The respiratory sensing device 1000 may independently process or correlate information received from another respiratory sensing device 1000 or an external device to perform related operations.

Also, the interface device 2000 may be connected to one or more blood pressure measuring apparatuses. For example, at least one of an upper arm blood pressure monitor 1950 and a wrist blood pressure monitor 1900 may be attached to a body part of the patient to which the respiratory sensing device is attached. In this case, the interface device 2000 may independently process or correlate blood pressure information received from the respiratory sensing device and blood pressure information received from the blood pressure measuring apparatus to perform related operations.

The interface device 2000 may be wired or wirelessly connected to one or more respiratory monitoring devices 3000. The interface device 2000 may transmit a respiratory signal of the patient 1 to the respiratory monitoring device 3000.

When the interface device 2000 is wirelessly connected to the respiratory monitoring device 3000, the interface device 2000 may use at least one of Bluetooth, Zigbee, and Wi-Fi to transmit a respiratory signal to the respiratory monitoring device 3000. It will be appreciated that the present invention is not limited to the above communication method and any method can be used without limitations as long as the method is capable of sending a respiratory signal in a wireless manner.

The interface device 2000 may include a battery 2100, a controller 2200, a first power cable 2120, a first communication cable 2220, and a communication module 2300.

The controller 2200 may be an element for receiving and processing an electric signal.

The controller 2200 may receive a piezoelectric signal, which is an electrical signal, from the sensing module 1400. In this case, the piezoelectric signal may be transmitted from the sensing module 1400 to the controller 2200 through a first communication cable 2220. The first communication cable 2220 may have one end connected to the piezoelectric film 1460 and another end connected to the controller 2200. A position at which the first communication cable 2220 is connected to the piezoelectric film 1460 will be described in detail with reference to FIGS. 19 and 20.

Since the controller 2200 and the piezoelectric film 1460 are connected to each other through the first communication cable 2200, the controller 2200 is physically separated from the piezoelectric film 1460. In this case, it is possible to reduce noise generated in the piezoelectric film 1460 by the controller 2200. That is, electric influence caused by the controller 2200 may not disturb the capacitance between both electrodes 1480a and 1480b. For example, when the controller 2200 overlaps the piezoelectric film 1460, the mass and volume of the controller 2200 may cause noise that may affect vibration sensing sensitivity of the piezoelectric film 1460. Also, the controller 2200 may be made of a rigid material because of general characteristics of a circuit board. At this time, the controller 2200, which is rigid, and the piezoelectric film 1460, which is flexible, may have different vibration response levels, and thus a gap may occur between the controller 2200 and the piezoelectric film 1460 during vibration. This gap may cause noise. Accordingly, by the controller 2200 and the piezoelectric film 1460 being remotely connected to each other using the first communication cable 2220, it is possible to reduce or remove the aforementioned potential noise causes.

The controller 2200 may include a circuit board.

The circuit board is an element for receiving and processing signals. Various electronic devices necessary for signal processing may be arranged in the circuit board. The circuit board may be made of a flexible material capable of being bent according to the curvature of the body and may be a general rigid printed circuit board (PCB). It will be appreciated that a flexible printed circuit board (FPCB) may be used as the circuit board.

The controller 2200 may perform operations necessary to process a received electric signal. For example, the controller 2200 may perform a noise removal process on the received electric signal and, to this end, may include a noise removal circuit.

Alternatively, the controller 2200 may perform impedance matching on the output of the sensing module 1400 and, to this end, may include an FET circuit.

Alternatively, the controller 2200 may perform an operation for amplifying the electric signal.

Subsequently, the controller 2200 may transmit the processed electric signal to the respiratory monitoring device 3000.

The battery 2100 may supply power necessary for operation of the controller 2200. In this case, the battery 2100 may supply power necessary for operation of the sensing module 1400 through a first power cable 2120. The first power cable 2120 may have one end connected to the battery and another end connected to the piezoelectric film 1460. A position at which the first power cable 2120 is connected to the piezoelectric film 1460 will be described in detail with reference to FIGS. 19 and 20.

The first power cable 2120 and the first communication cable 2220 may be provided as separate independent cables. Also, the first power cable 2120 and the second power cable 2220 may be designed to have a cable assembly structure and thus may have separate electric wires but be provided as a single line.

The communication module 2300 may transmit a respiratory signal to an external device. In this case, the communication module 2300 may transmit the respiratory signal to the respiratory monitoring device 3000. The communication module 2300 may transmit the respiratory signal to the respiratory monitoring device 3000 in a wired manner by cable. Also, the communication module 2300 may transmit the respiratory signal to the respiratory monitoring device 3000 in a wireless manner by means of at least one of Bluetooth, Zigbee, and Wi-Fi.

The structure and elements of the respiratory sensing device 1000 according to an embodiment of the present invention will be described below with reference to FIGS. 4 to 7 and 18 to 21.

Figure 4:
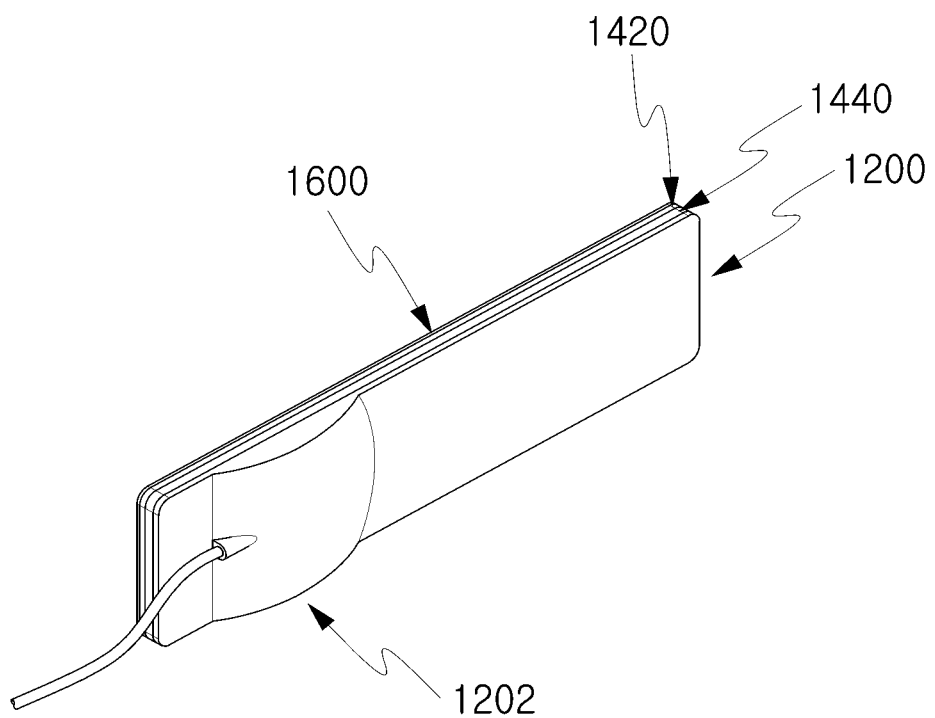
FIG. 4 is a perspective view of a respiratory sensing device according to an embodiment of the present invention.
Figure 5:
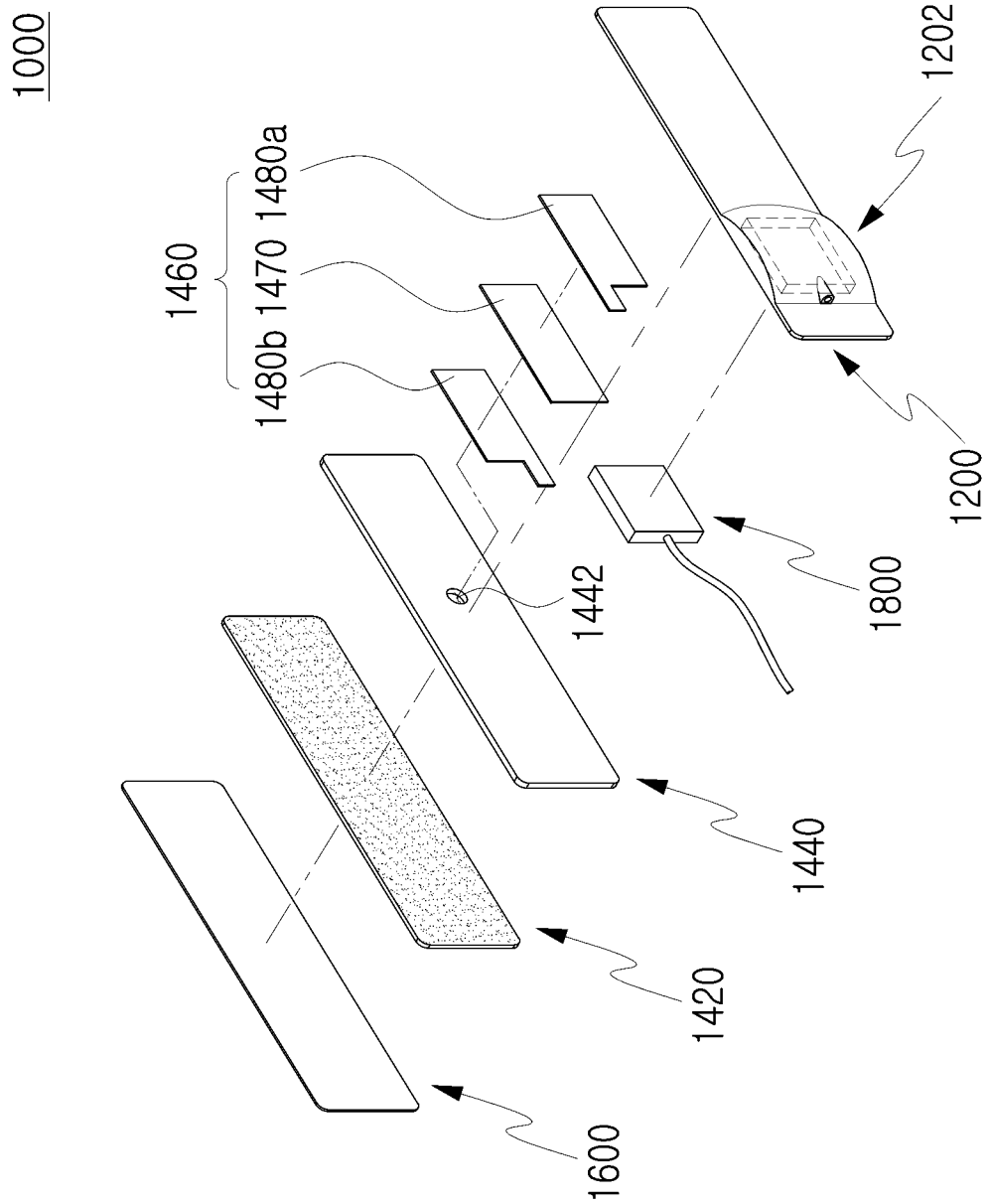
FIG. 5 is an exploded perspective view of a respiratory sensing device according to an embodiment of the present invention.
Figure 6:
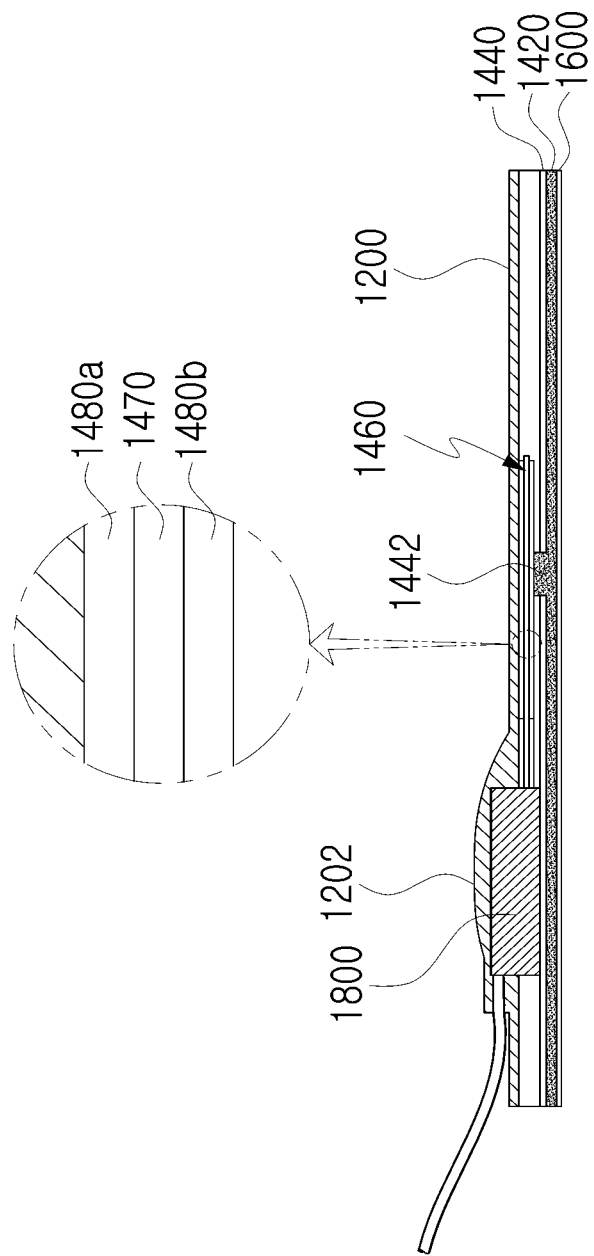
FIG. 6 is a side cross-sectional view of a respiratory sensing device according to an embodiment of the present invention.
Figure 7:
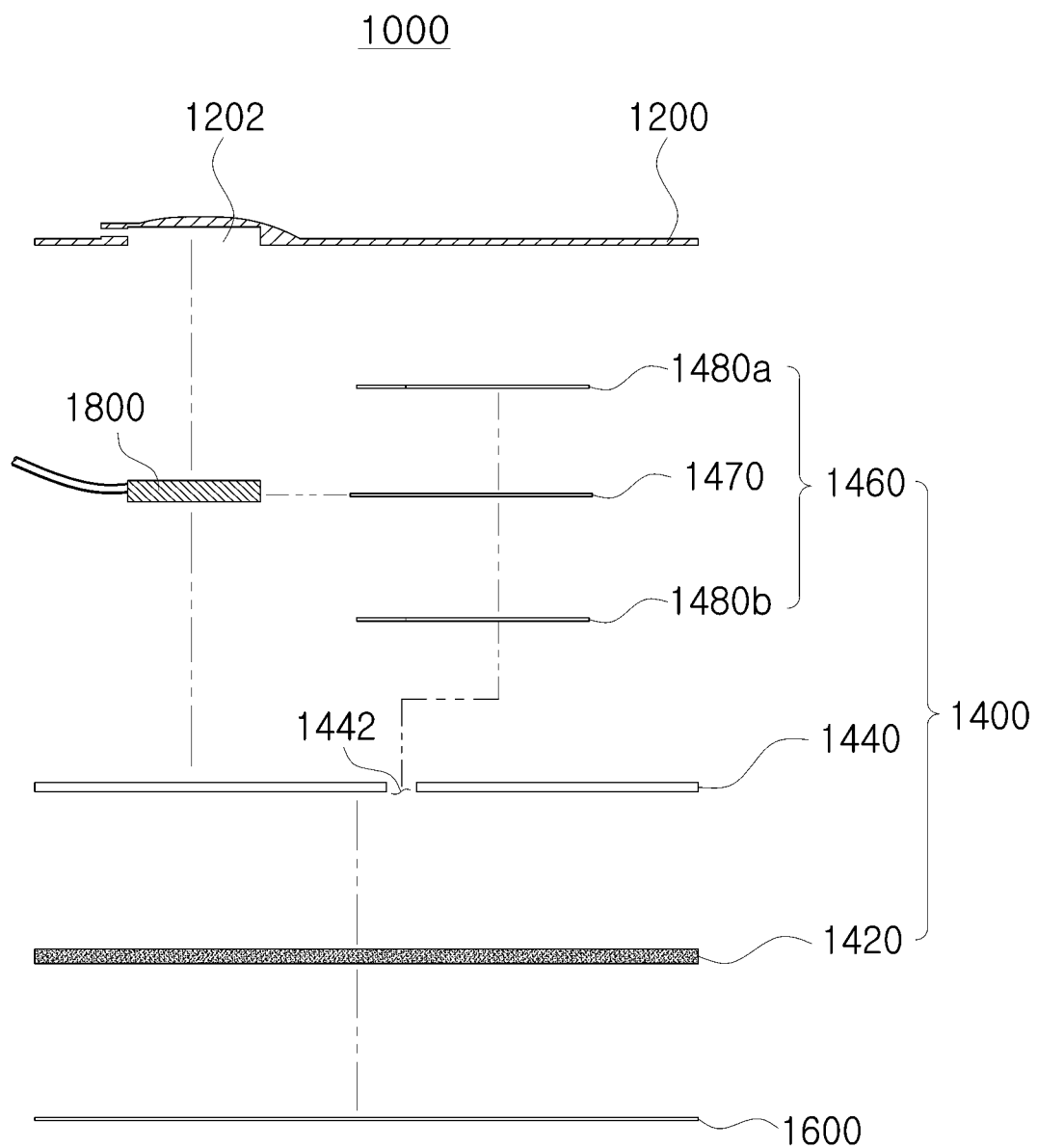
FIG. 7 is an exploded side cross-sectional view of a respiratory sensing device according to an embodiment of the present invention.

FIG. 4 is a perspective view of the respiratory sensing device 1000 according to an embodiment of the present invention, FIG. 5 is an exploded perspective view of the respiratory sensing device 1000 according to an embodiment of the present invention, FIG. 6 is a side cross-sectional view of the respiratory sensing device 1000 according to an embodiment of the present invention, and FIG. 7 is an exploded side cross-sectional view of the respiratory sensing device 1000 according to an embodiment of the present invention.

Figure 18:
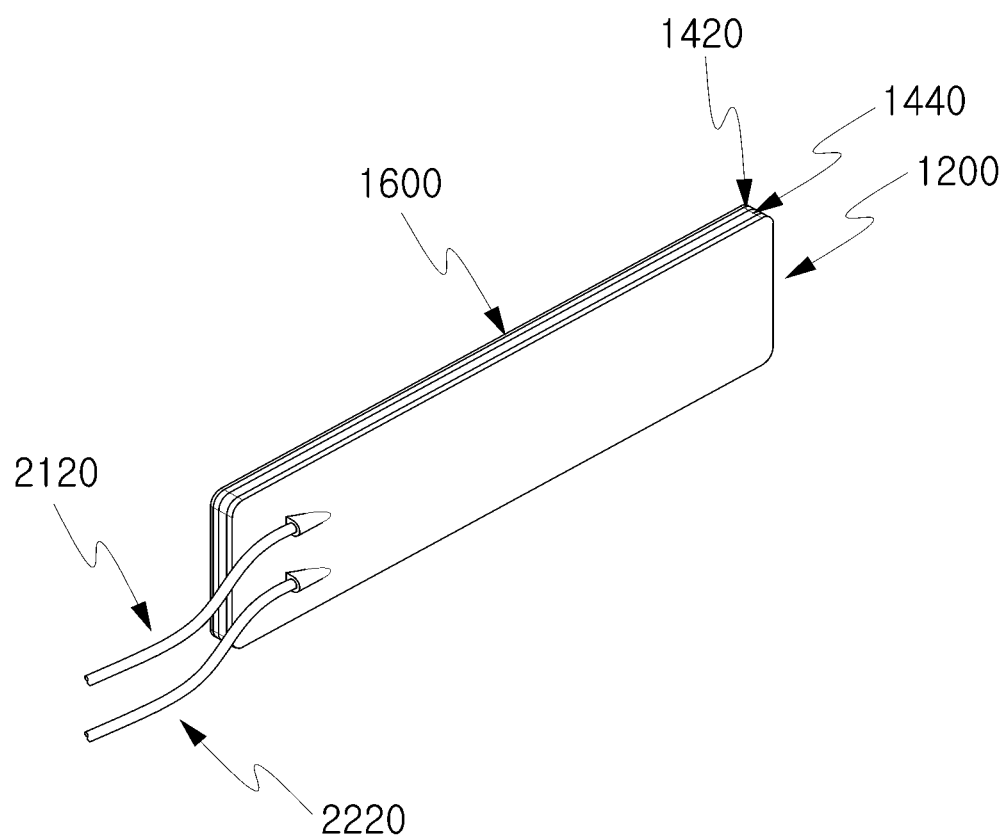
FIG. 18 is another perspective view of a respiratory sensing device according to an embodiment of the present invention.
Figure 19:
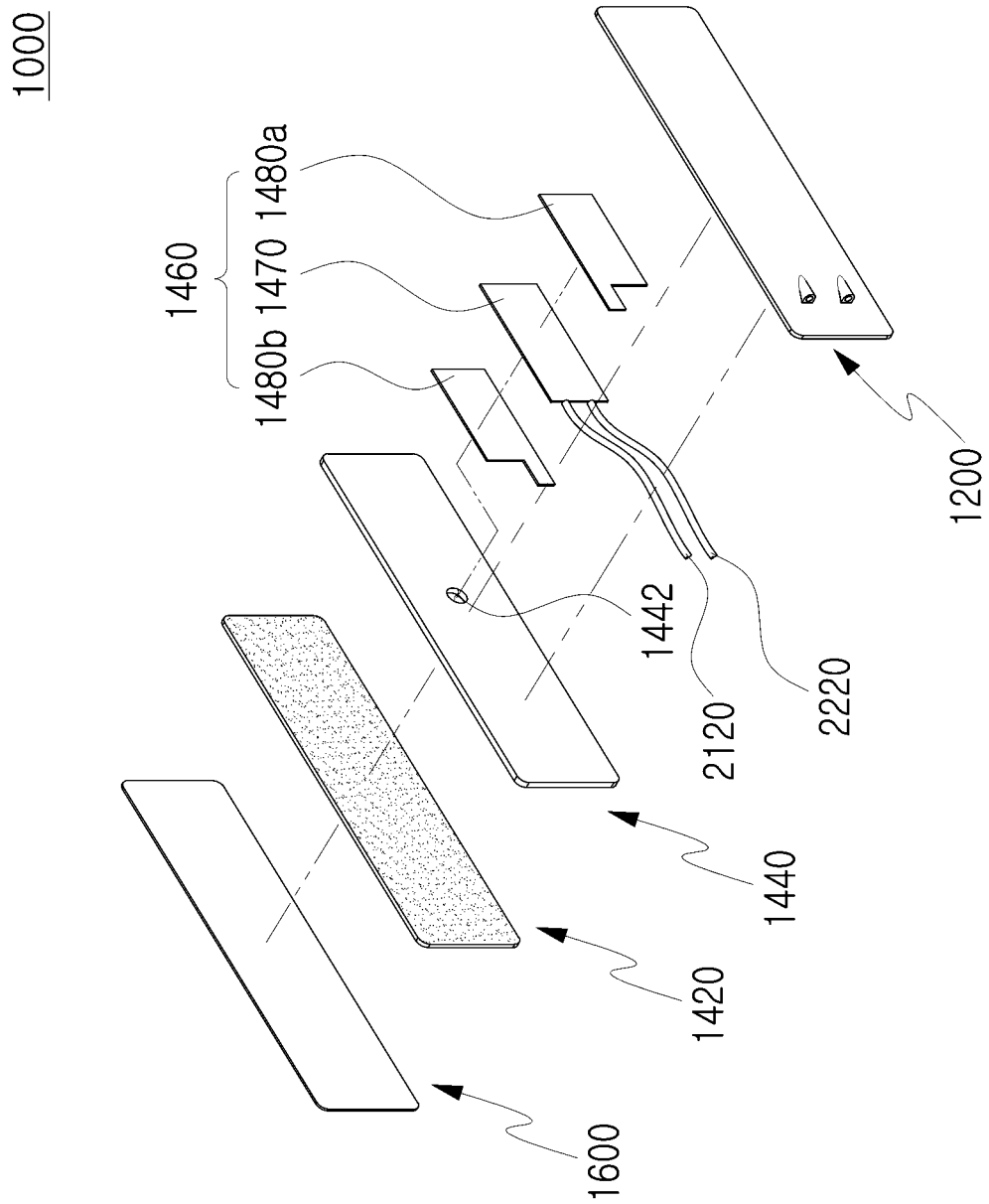
FIG. 19 is another exploded perspective view of a respiratory sensing device according to an embodiment of the present invention.
Figure 20:
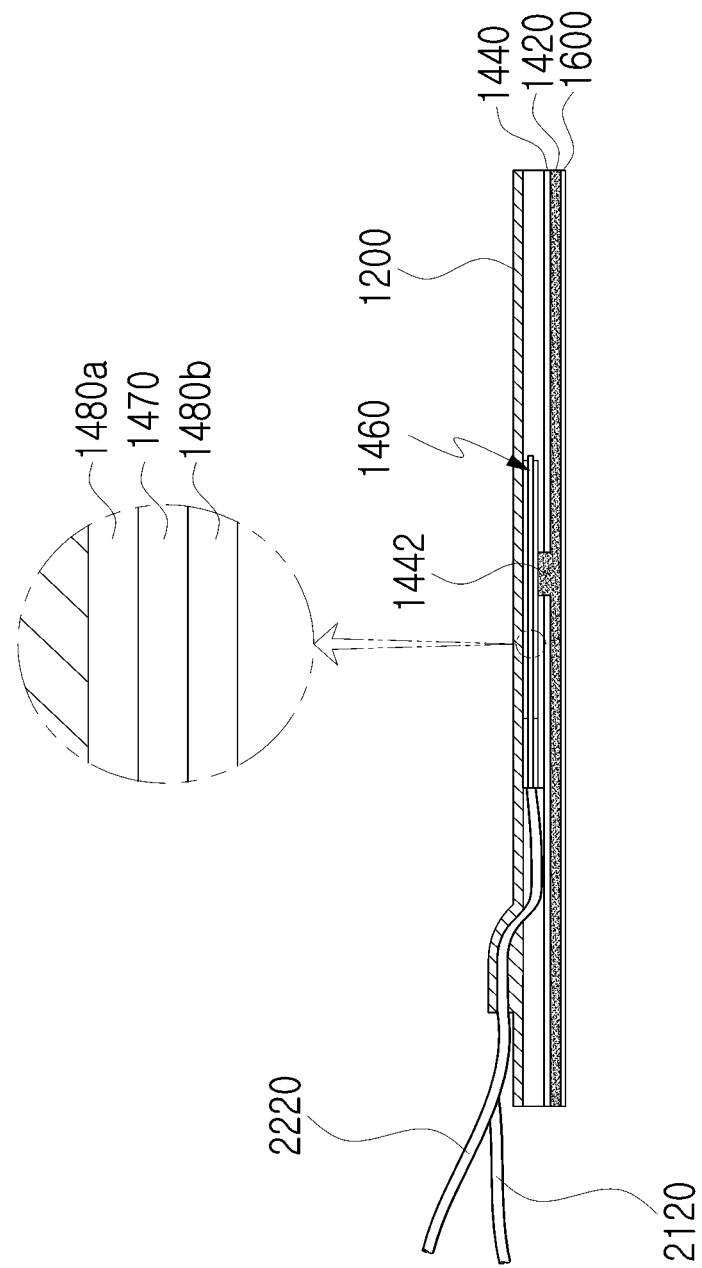
FIG. 20 is another side cross-sectional view of a respiratory sensing device according to an embodiment of the present invention.
Figure 21:
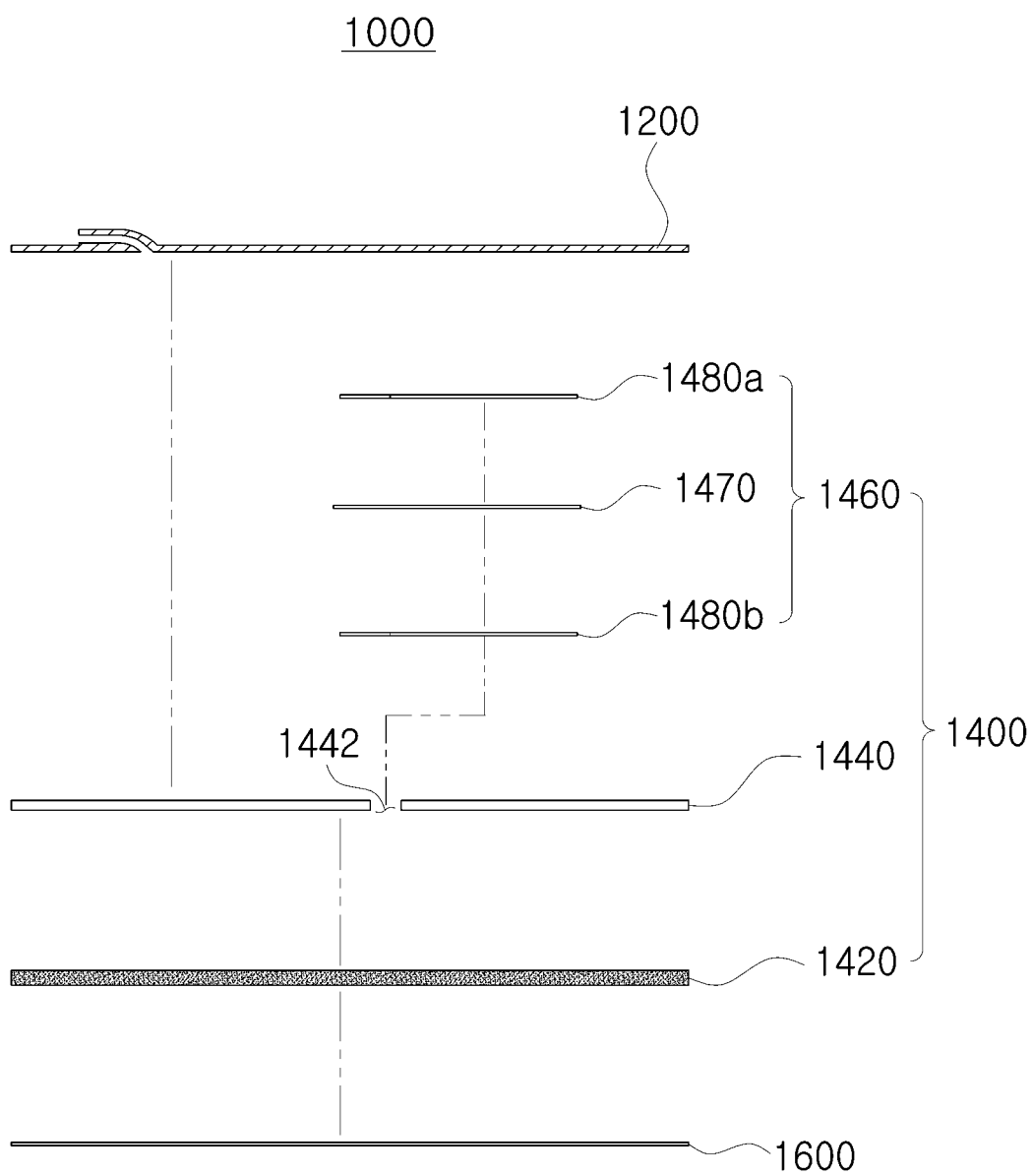
FIG. 21 is another exploded side cross-sectional view of a respiratory sensing device according to an embodiment of the present invention.

FIG. 18 is another perspective view of the respiratory sensing device according to an embodiment of the present invention, FIG. 19 is another exploded perspective view of the respiratory sensing device according to an embodiment of the present invention, FIG. 20 is another side cross-sectional view of the respiratory sensing device according to an embodiment of the present invention, and FIG. 21 is another exploded side cross-sectional view of the respiratory sensing device according to an embodiment of the present invention.

The respiratory sensing device 1000 may be in the form of a generally thin flat plate when viewed from the outside.

The respiratory sensing device 1000 may be produced in the form of a quadrangle when viewed from the top. Specifically, the respiratory sensing device 1000 may be in the form of a rectangle having a longer end so as to cover the attachment site 2.

One region of an upper portion of the respiratory sensing device 1000 may protrude upward. The protruding shape may be formed at a position laterally biased from the respiratory sensing device 1000.

A cable may be connected to one side of the respiratory sensing device 1000. One region of the upper portion of the respiratory sensing device 1000 may protrude upward due to protrusion of the cable. Although the first power cable 2120 and the first communication cable 2220 are separately shown in FIGS. 18 to 20, the first power cable 2120 and the first communication cable 2220 may be designed in the form of a cable assembly and be provided as a single line.

The respiratory sensing device 1000 may have a structure in which the cover 1600, the adhesive layer 1420, the insulating film 1440, the piezoelectric film 1460, and the case 1200 are sequentially stacked in order from the lowest layer to the highest layer. In this case, the signal processing module 1800 may be placed horizontally with the piezoelectric film 1460 and placed between the insulating film 1440 and the case 1200. That is, the respiratory sensing device 1000 may be a structure in which the cover 1600 is placed in the lowest layer, the adhesive layer 1420 is placed over the cover 1600, the piezoelectric film 1460 and the signal processing module 1800 are placed over the adhesive layer 1420, and the case 1200 is placed in the highest layer.

In this case, the respiratory sensing device 1000 may be a structure in which the cover 1600, the insulating film 1440, the piezoelectric film 1460, and the case 1200 are sequentially stacked in the order from the lowest layer to the highest layer.

That is, the respiratory sensing device 1000 may be a structure in which the cover 1600 is placed in the lowest layer, the piezoelectric film 1460 is placed over the cover 1600, and the case 1200 is placed in the highest layer.

The respiratory sensing device 1000 may further include the adhesive layer 1420. In this case, the adhesive layer 1420 may be placed over the cover 1600, and the piezoelectric film 1460 may be placed over the adhesive layer 1420.

The cover 1600 may be provided in the form of a thin film. The cover 1600 may have an area greater than or equal to the area of the adhesive layer 1420 when viewed from the top.

The adhesive layer 1420 may be provided in the form of a thin film. The adhesive layer 1420 may be provided as a gel-like material having all of adhesiveness, conductivity, and flexibility. Here, as an example of the gel-like material, a hydrogel may be used. An example of the hydrogel may be an agarose gel. A gel is a material having a porous network structure, and its shape can be flexibly changed by an external force. Also, a hydrogel may have electrical conductivity because it has a network structure containing water. Also, a gel may have adhesiveness due to cross-linking that forms the network structure.

The adhesive layer 1420 may have a sufficient length to provide sufficient adhesion to the respiratory sensing device 1000. In particular, the adhesive layer 1420 may be placed in an upper layer and may extend a sufficient length toward both sides of a housing part 1202 in which the signal processing module 1800 is housed in order to accurately bond the cable and the signal processing module 1800, which may be relatively heavy.

A gel-like material forming the adhesive layer 1420 may have an electrical channel function for grounding a lower electrode 1480*b* and a respiratory vibration filtering function in addition to a function of adhering the respiratory sensing device 1000 to the attachment site 2.

The insulating film 1440 may be provided in the form of a thin film. The insulating film 1440 may be interposed between the adhesive layer 1420 and the piezoelectric film 1460. The area of the insulating film 1440 may be greater than the area of the piezoelectric film 1460 when viewed from the top.

The manufacturing material or the manufacturing specifications such as thickness and area of the insulating film 1440 may be determined in consideration of the insulation, flexibility, vibration transfer rate, and the like of the insulating film 1440.

A through-hole 1442 may be formed in the insulating film 1440. The through-hole 1442 is an element for grounding the piezoelectric film 1460 to a human body through the adhesive layer 1420 by electrically connecting the piezoelectric film 1460 and the adhesive layer 1420.

The through-hole 1442 may be an empty space extending from an upper surface to a lower surface of the insulating film 1440 through the insulating film 1440.

When the adhesive layer 1420, the insulating film 1440, and the piezoelectric film 1460 are piled up, the through-hole 1442 may be formed in one region of the insulating film 1440 which is in contact with the adhesive layer 1420 and the piezoelectric film 1460. Thus, when the adhesive layer 1420, the insulating film 1440, and the piezoelectric film 1460 are closely piled up, a portion of the adhesive layer 1420 corresponding to the through-hole 1442 may be inserted into the through-hole 1442 and thus be brought into contact with the lower electrode 1480*b* of the piezoelectric film 1460 (see FIG. 6). Thus, the piezoelectric film 1460 and the adhesive layer 1420 may be electrically connected to each other in the region corresponding to the through-hole 1442.

The through-hole 1442 may be a cylinder having a generally circular cross-section but is not limited thereto.

The through-hole 1442 may have a polygonal cross-section or may be provided in the form of a slit having a minimal cross-section.

The piezoelectric film 1460 may include a piezoelectric material 1470, an upper electrode 1480a, and a lower electrode 1480b. The piezoelectric material 1470, the upper electrode 1480a, and the lower electrode 1480b may be provided in the form of a thin film. The upper electrode 1480a may be formed on an upper surface of the piezoelectric material 1470, and the lower electrode 1480b may be formed on a lower surface of the piezoelectric material 1470.

The structure and elements of the piezoelectric film 1460 will be described below in more detail.

The signal processing module 1800 may be placed close to the piezoelectric film 1460. This is because it is advantageous for the signal processing module 1800 to be placed close to an output terminal for the purpose of impedance matching. When a path for connecting the signal processing module 1800 to the piezoelectric film 1460 is long, the output power and sensitivity of the electric signal output from the piezoelectric film 1460 may be reduced. All materials have their own inherent impedances, and as the connection path becomes longer, the impedance increases and thus the electric signal output from the piezoelectric film 1460 may become more vulnerable to noise.

The signal processing module 1800 may be placed in parallel to the piezoelectric film 1460 when viewed from the top. In other words, the signal processing module 1800 may be placed such that it does not overlap the piezoelectric film 1460 when viewed from the top. This is to prevent electric influence caused by the signal processing module 1800 from disturbing the capacitance between both of the electrodes 1480a and 1480b by not placing the signal processing module 1800 toward a gap between the upper electrode 1480a and the lower electrode 1480b.

In this case, it is possible to remove noise generated due to overlapping between the signal processing module 1800 and the piezoelectric film 1460. For example, when the signal processing module 1800 and the piezoelectric film 1460 overlap each other, the mass and volume of the signal processing module 1800 may cause noise that may affect vibration sensing sensitivity of the piezoelectric film 1460. Also, the signal processing module 1800 may be made of a rigid material because of general characteristics of a circuit board. At this time, the signal processing module 1800, which is rigid, and the piezoelectric film 1460, which is flexible, may have different vibration response levels, and thus a gap may occur between the signal processing module 1800 and the piezoelectric film 1460 during vibration. This gap may cause noise. Accordingly, by the signal processing module 1800 and the piezoelectric film 1460 being horizontally placed in parallel so as to not overlap each other, it is possible to reduce or remove the aforementioned potential noise causes.

The signal processing module 1800 may include a circuit board, a connection terminal, a cable, and a housing.

The circuit board is an element for receiving and processing signals. Various electronic devices necessary for signal processing may be arranged in the circuit board. The circuit board may be made of a flexible material capable of being bent according to the curvature of the body and may be a general rigid PCB. It will be appreciated that an FPCB may be used as the circuit board.

The connection terminal may be connected to the piezoelectric film 1460 to receive electric signals from the piezoelectric film 1460. In this case, the connection terminal may be combined with a terminal part 1484 of the piezoelectric film 1460 through riveting. Alternatively, the connection terminal may be combined with the terminal part 1484 of the piezoelectric film 1460 through soldering. Alternatively, a conducting wire connected to the terminal part 1484 of the piezoelectric film 1460 may be connected to the connection terminal.

The cable is an element for transmitting signals processed in the circuit board to the respiratory monitoring device 3000. The cable may be horizontally inserted into a housing at one side and may be connected to the circuit board. The cable may approach the signal processing module 1800 by extending from a side away from the piezoelectric film 1460 so as to not cross the piezoelectric film 1460.

The housing is an element for providing a space in which the circuit board, the connection terminal, and the cable are to be placed. The housing may be a cover member for protecting the circuit board, the connection terminal, and the cable. Thus, the connection between the circuit board, the connection terminal, and the cable in the housing may be kept firm even against an external vibration.

Also, the housing may have a shape in which it is easy for the circuit board to be interposed between the case 1200 and the insulating film 1440. For example, the housing may be formed in the shape of a flat plate so that it can be easily fixed.

Also, the housing may block electric signals so that the internal components, except for the connection terminal, are not electrically connected to an external element. Accordingly, the housing may be made of an insulator.

The circuit board may be connected in parallel to the terminal part 1484 of the piezoelectric film 1460 at one side of the housing.

The case 1200 may be placed on the highest surface of the respiratory sensing device 1000. The case 1200 may be generally formed as a thin film. The case 1200 may have an area greater than or equal to the area of the insulating film 1440 when viewed from the top. The case 1200 may cover the insulating film 1440, and the piezoelectric film 1460 and the signal processing module 1800 may be interposed therebetween.

The case 1200 may have a housing part 1202 in which the signal processing module 1800 is housed. The housing part 1202 may have a shape in which one region of the case 1200 protrudes upward convexly and an empty space exists therein. When the case 1200 and the piezoelectric film 1460 are piled up, the housing part 1202 may be formed at a side of the piezoelectric film 1460 so that the housing part 1202 does not overlap the piezoelectric film 1460. In consideration of the housing part 1202, the adhesive layer 1420 may extend from one side of the housing part 1202 by a predetermined length in a direction away from the piezoelectric film 1460. A hole through which a cable is to pass may be formed in the housing part 1202. Referring to FIGS. 19 to 21, the hole through which the cable is to pass is formed on an upper end of the case 1200 but may be formed on a side surface of the case 1200.

The piezoelectric film 1460 will be described below in detail with reference to FIGS. 8 to 10.

Figure 8:
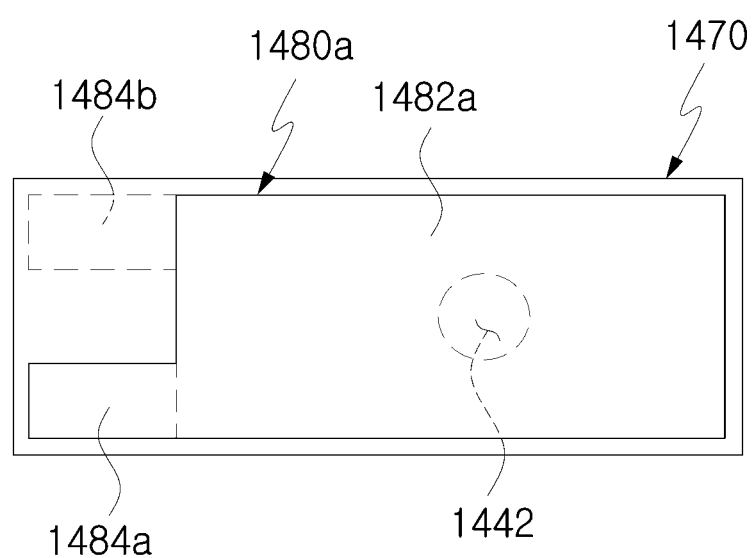
FIG. 8 is a top view of a piezoelectric film according to an embodiment of the present invention.
Figure 9:
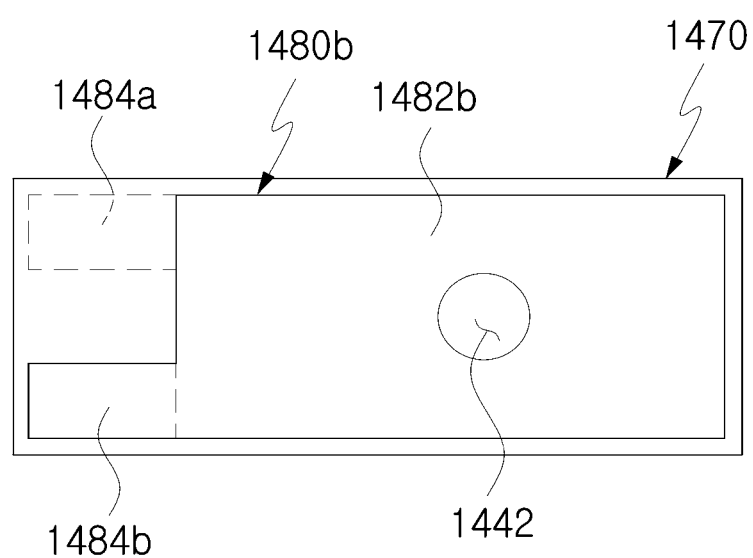
FIG. 9 is a rear view of a piezoelectric film according to an embodiment of the present invention.
Figure 10:
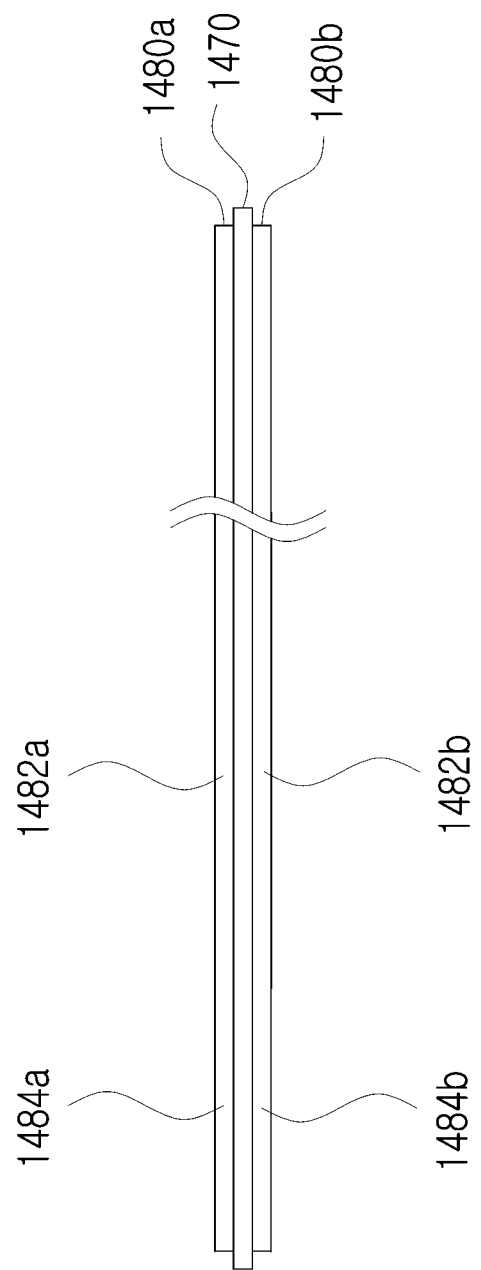
FIG. 10 is a side view of a piezoelectric film according to an embodiment of the present invention.

FIG. 8 is a top view of the piezoelectric film 1460 according to an embodiment of the present invention, FIG. 9 is a rear view of the piezoelectric film 1460 according to an embodiment of the present invention, and FIG. 10 is a side view of the piezoelectric film 1460 according to an embodiment of the present invention.

The piezoelectric film 1460 may include a piezoelectric material 1470, an upper electrode 1480a stacked on an upper surface of the piezoelectric material 1470, and a lower electrode 1480*b* formed on a lower surface of the piezoelectric material 1470. The upper electrode 1480*a* and the lower electrode 1480*b* may entirely or partially cover the upper surface and the lower surface of the piezoelectric material 1470, respectively.

The upper electrode 1480*a* and the lower electrode 1480*b* may have the same area, thickness, form, and material or different areas, thicknesses, forms, and materials.

The piezoelectric material 1470 may be in the form of a quadrangular thin film.

Both of the electrodes 1480*a* and 1480*b* may be formed to include a quadrangular body and a region extending outward from one side of the quadrangle when viewed from the top.

Each of the electrodes 1480*a* and 1480*b* may include a facing part 1482, a grounding part 1486, and a terminal part 1484.

The facing parts 1482 refer to one regions of the electrodes 1480*a* and 1480*b* in which the electrodes 1480*a* and 1480*b* face each other with the piezoelectric material 1470 interposed therebetween when the electrodes 1480*a* and 1480*b* are stacked on the piezoelectric material 1470. The facing parts 1482 of the electrodes 1480*a* and 1480*b* may be in direct contact with the piezoelectric material 1470.

A structure in which the facing part 1482*a* of the upper electrode 1480*a*, the piezoelectric material 1470, and the facing part 1482*b* of the lower electrode 1480*b* are stacked to overlap one another forms a sensing region of the piezoelectric film 1460. The sensing region is a region which exhibits a behavior similar to that of a capacitor and where a vibration is actually sensed by the piezoelectric effect and a corresponding voltage is generated. The sensing region may be placed at a location where the piezoelectric effect occurs most effectively in response to the vibration transferred to the piezoelectric film 1460.

The sensing region may be placed anywhere on the piezoelectric film 1460 as long as the piezoelectric effect can be maximized. For example, the sensing region may be placed at the center of the piezoelectric film 1460 to sense bending of the piezoelectric film 1460 well.

The sensing region may be provided with a certain degree of tension to keep the piezoelectric film 1460 flat. The tension may affect sensitivity improvement of the piezoelectric film 1460.

The terminal part 1484 is a region which is electrically connected to the connection terminal of the signal processing module 1800. Thus, the terminal part 1484 may electrically connect the sensing region and the signal processing module 1800 and may transmit a voltage and an electric signal generated in the sensing region to the signal processing module 1800.

The terminal part 1484 may be electrically connected to the first communication cable 2220 of the interface device 2000. That is, the terminal part 1484 may be connected to the controller 2200 of the interface device 2000 through the first communication cable 2220. Thus, the terminal part 1484 may electrically connect the sensing region and the controller 2200 and transmit a voltage and a piezoelectric signal generated in the sensing region to the controller 2200.

The terminal part 1484*a* of the upper electrode, the piezoelectric material 1470, and the terminal part 1484*b* of the lower electrode may not be overlappingly stacked when viewed from a direction vertical to a main surface of the piezoelectric film 1460. For example, the terminal parts 1484 of the electrodes 1480*a* and 1480*b* may not have the piezoelectric material 1470 interposed therebetween or may be placed in different regions.

The terminal parts 1484 may extend outward from the facing parts 1482. The terminal part 1484*a* of the upper electrode 1480*a* and the terminal part 1484*b* of the lower electrode 1480*b* may extend toward the same side of the piezoelectric film 1460. The direction in which the terminal parts 1484 extend may be a direction toward the signal processing module 1800. In this case, the terminal part 1484*a* of the upper electrode 1480*a* and the terminal part 1484*b* of the lower electrode 1480*b* may extend from the same side surface but from different parts of the side surface. For example, when the terminal part 1484*a* of the upper electrode 1480*a* extends from a left region of one side of the facing part 1482*a*, the terminal part 1484*b* of the lower electrode 1480*b* may extend from a right region of the one side of the facing part 1482*b*. This may make it easier for the terminal parts 1484 of the electrodes 1480*a* and 1480*b* to be connected to the signal processing module 1800.

The terminal parts 1484 may extend outward from the facing parts 1482. The terminal part 1484*a* of the upper electrode 1480*a* and the terminal part 1484*b* of the lower electrode 1480*b* may extend toward the same side of the piezoelectric film 1460. The direction in which the terminal parts 1484 extend may be a direction in which the first communication cable 2220 passes. In this case, the terminal part 1484*a* of the upper electrode 1480*a* and the terminal part 1484*b* of the lower electrode 1480*b* may extend from the same side surface but from different parts of the side surface. For example, when the terminal part 1484*a* of the upper electrode 1480*a* extends from a left region of one side of the facing part 1482*a*, the terminal part 1484*b* of the lower electrode 1480*b* may extend from a right region of the one side of the facing part 1482*b*. This may make it easier for the terminal parts 1484 of the electrodes 1480*a* and 1480*b* to be connected to the first communication cable 2220. Also, this may make it easier for the terminal parts 1484 of the electrodes 1480*a* and 1480*b* to be connected to the first power cable 2120.

The grounding part 1486 is a region for grounding the piezoelectric film 1460. Most of the piezoelectric film 1460 is insulated by the insulating film 1440, but may not be insulated at the grounding part 1486. By the lower electrode 1480*b* being electrically connected to a large electrical capacity object through the grounding part 1486, it is possible to acquire electrical stability.

The grounding part 1486 may be formed in one region of the lower electrode 1480*b*. When the piezoelectric film 1460 and the insulating film 1440 are piled up, the grounding part 1486 may be one region of the lower electrode 1480*b* positionally corresponding to the through-hole 1442 of the insulating film 1440. Since the through-hole 1442 forms an empty space by passing through the upper surface and lower surface of the insulating film 1440, the grounding part 1486 corresponding to the through-hole 1442 may not be insulated.

There are various points to which the grounding part 1486 is to be electrically connected. For example, a part to which the grounding part 1486 is electrically connected may be the skin of the patient 1. Alternatively, a part to which the grounding part 1486 is electrically connected may be the adhesive layer 1420 connected to the skin of the patient 1. Alternatively, a part to which the grounding part 1486 is electrically connected may be the ground. Alternatively, a part to which the grounding part 1486 is electrically connected may be an external device with a large electric capacity and a preset reference potential.

The grounding part 1486 may be one region of the terminal part 1484 or one region of the facing part 1482.

A respiratory sensing operation of the respiratory sensing device 1000 according to an embodiment of the present invention will be described below.

Figure 11:
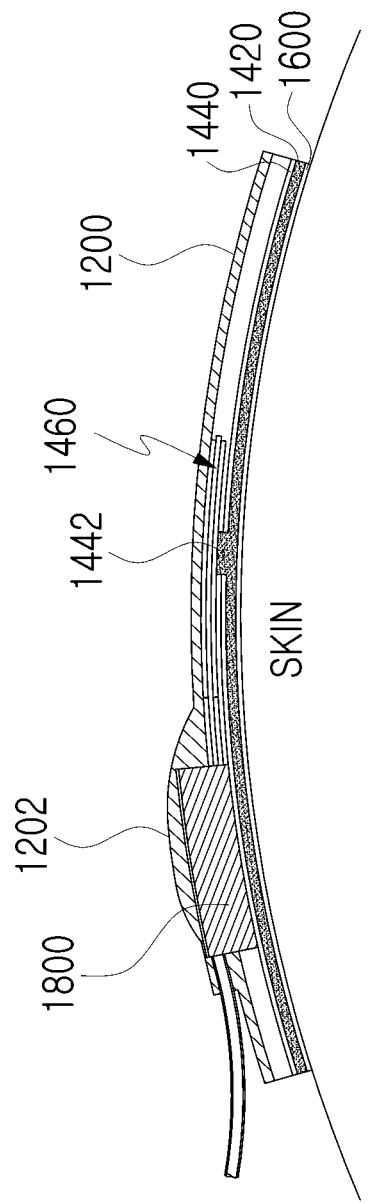
FIG. 11 is a diagram showing a respiratory sensing operation of a respiratory sensing device according to an embodiment of the present invention.
Figure 22:
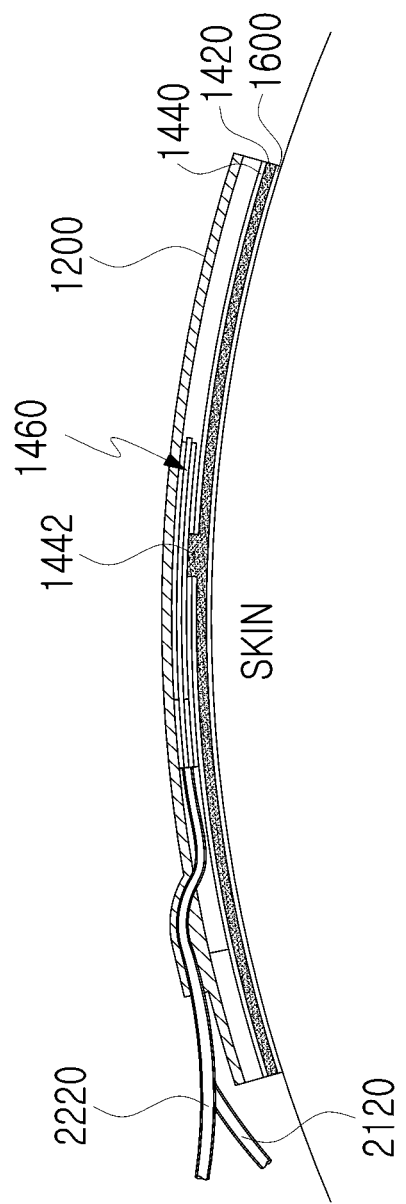
FIG. 22 is another diagram showing a respiratory sensing operation of a respiratory sensing device according to an embodiment of the present invention.

FIG. 11 is a diagram showing a respiratory sensing operation of the respiratory sensing device 1000 according to an embodiment of the present invention, and FIG. 22 is another diagram showing a respiratory sensing operation of the respiratory sensing device according to an embodiment of the present invention.

In the respiratory sensing device 1000 that is actually attached to the attachment site 2 and is fully coupled, a path through which a vibration generated due to respiration is transferred to the piezoelectric film 1460 via each layer and roles of elements for improving sensing sensitivity of the respiratory sensing device 1000 will be described with reference to FIG. 11 as follows.

First, a process in which the vibration is transferred and converted into electrical signals will be described.

The respiratory sensing device 1000 may be adhered to (pressed against) the attachment site 2 via the adhesive layer 1420. The vibration generated due to respiration may be transferred to the adhesive layer 1420. In this case, as described above, the adhesive layer 1420 may be in the form of a gel. For example, the adhesive layer 1420 may be a kind of hydrogel, that is, an agarose gel. As described above, the gel may change in form according to the curvature of the attachment site 2 and be adhered to the attachment site 2 with the greatest surface area. As will be described in more detail below, the gel can selectively allow only a vibration generated due to respiration to be transmitted to an upper layer. Other vibrations are a kind of noise and may be blocked by the gel from being transferred.

The vibration due to respiration that has passed through the gel may be transferred to the piezoelectric film 1460 through the insulating film 1440. In this case, the insulating film 1440 is also flexibly bent so that the insulating film 1440 may be closely adhered to the adhesive layer 1420, which is placed on the lower surface, and the piezoelectric film 1460, which is placed on the upper surface, without gaps.

The vibration generated due to respiration may be transferred to the piezoelectric film 1460 through the insulating film 1440. The piezoelectric film 1460 receives an external force caused by the vibration, and thus a voltage is generated between the upper electrode 1480*a* and the lower electrode 1480*b* of the sensing region. In this case, the grounding part 1486 in the lower electrode 1480*b* may be electrically connected to the adhesive layer 1420 through the through-hole 1442. A generated electrical signal may be transmitted to the signal processing module 1800 through the terminal part 1484.

Also, a vibration generated due to respiration may be transferred to the piezoelectric film 1460 through the insulating film 1440. The piezoelectric film 1460 receives an external force caused by the vibration, and thus a voltage is generated between the upper electrode 1480*a* and the lower electrode 1480*b* of the sensing region. In this case, the grounding part 1486 in the lower electrode 1480*b* may be electrically connected to the adhesive layer 1420 through the through-hole 1442. A piezoelectric signal, which is the generated electric signal, may be transmitted to the first communication cable 2220 through the terminal part 1484. That is, the generated piezoelectric signal may be transmitted to the controller 2200 of the interface device 2000 through the first communication cable 2220.

In this case, the roles of the adhesive layer 1420 and the insulating film 1440 contributing to sensing sensitivity improvement will be described as follows.

The insulating film 1440 may insulate the piezoelectric film 1460 by covering the surface area of the piezoelectric film 1460, thus minimizing the influence of electromagnetic waves radiated from a human body.

Since the vibration due to respiration is a fine vibration, very precise sensing sensitivity is required. Therefore, even if the magnitude of the electromagnetic waves radiated from the human body is small, the electromagnetic waves may influence respiratory sensing sensitivity, and the influence may be further exacerbated as the area in which the human body surface and the piezoelectric film 1460 are electrically connected to each other increases.

In detail, the piezoelectric material 1470 having the electrodes 1480*a* and 1480*b* attached to the upper and lower surfaces may exhibit a behavior similar to that of a kind of capacitor. That is, when the piezoelectric effect occurs, an electromagnetic field may be generated in a direction from the upper electrode 1480*a* to the lower electrode 1480*b* or vice versa. Considering the attachment form of the respiratory sensing device 1000, the direction of the electromagnetic field may coincide with the direction of the electronic magnetic waves radiated from the human body. This may exacerbate the adverse effect of the electromagnetic waves radiated from the human body on the piezoelectric effect.

As a solution to this problem, by the insulating film 1440 minimizing a region of the piezoelectric film 1460 exposed to the human body surface (exposing only a region for the through-hole for grounding), it is possible to effectively block electromagnetic waves radiated from the human body.

Meanwhile, by the piezoelectric film 1460 being grounded to the adhesive layer 1420 or the human body through the through-hole 1442 provided in the insulating film 1440, it is possible to increase sensing sensitivity.

Since the human body has a relatively huge electric capacity, it is possible to grant electrical stability to the respiratory sensing device 1000. Also, through the grounding, the piezoelectric film 1460 may set a reference potential.

Since the grounding to the human body is satisfied by an electrical connection, the grounding effect may occur irrespective of the area of the grounded region. However, when the through-hole for grounding is enlarged as described above, the influence of the electromagnetic waves radiated from the human body may be increased. Therefore, it may be advantageous to minimize the area of the through-hole.

Also, as aforementioned, the vibration transferred by the adhesive layer 1420 to an upper layer may be selective. The adhesive layer 1420 may allow a certain frequency vibration to be selectively transmitted and may block another certain frequency vibration. That is, the adhesive layer 1420 may be utilized as a band pass filter. In other words, impedance matching may be performed between the adhesive layer 1420 and skin in order to prevent reflection and loss of a vibration transferred from the skin. In particular, since a gel is ductile jelly-like material, the gel may tend to transmit vibrations with particular frequencies and absorb vibrations with the other particular frequencies by weakening a transfer force.

The frequencies of the vibrations transferred or blocked by the adhesive layer 1420 may be determined by material properties of the adhesive layer 1420 or manufacturing properties, such as thickness and area, of the adhesive layer 1420. Accordingly, the material and manufacturing specifications of the adhesive layer 1420 may be determined in consideration of a vibration frequency to be sensed and a vibration frequency of noise. For example, the thickness of the adhesive layer 1420 may be optimally designed so that a respiratory vibration frequency can be effectively transferred to an upper layer and also a respiration-independent vibration frequency can be effectively blocked. As another example, the component of the adhesive layer 1420 may be designed in consideration of an optimized component and an optimized ratio of components so that a respiratory vibration frequency can be effectively transferred to an upper layer and also a respiration-independent vibration frequency can be effectively blocked.

The vibration allowed or transferred by the adhesive layer 1420 may be a vibration to be sensed by the respiratory sensing device 1000. For example, when the respiratory sensing device 1000 is attached to a laryngeal prominence and configured to sense a vibration of the laryngeal prominence during respiration, the vibration transmitted and transferred by the adhesive layer 1420 may be a vibration of the laryngeal prominence generated during respiration.

The vibration blocked by the adhesive layer 1420 may be noise irrelevant to the vibration to be sensed by the respiratory sensing device 1000. For example, when the respiratory sensing device 1000 is attached to a laryngeal prominence and configured to sense a vibration of the laryngeal prominence during respiration, the noise may be a vibration irrelevant to the respiration. In detail, the noise may be a vibration generated by an endoscope and surgical instruments that unintentionally touch an airway while passing through the airway. Alternatively, the noise may be a vibration generated when the patient 1 swallows his/her saliva. Alternatively, the noise may be a vibration generated when the patient 1 suddenly moves.

As described above, the adhesive layer 1420 may have a sufficient length to provide sufficient adhesion to the respiratory sensing device 1000 and may be adhered to the attachment site 2. For example, when the adhesive layer 1420 is attached to a human body, the adhesive layer 1420 may be attached to a target region, in which a respiratory vibration to be actually sensed is generated, and also its periphery. Here, the adhesive layer 1420 being attached to the periphery is to provide stronger adhesion to the respiratory sensing device 1000. Sometimes, however, the periphery may provide noise to a vibration signal to be sensed. This is because a movement irrelevant to respiration or a movement relevant to respiration but with less reliability may occur in the periphery. The movement generated in the periphery may be transferred to the piezoelectric film 1460 through the adhesive layer 1420 and may act as noise.

To solve this problem, the adhesive layer 1420 may have a region where an adhesive material is applied and a region where no adhesive material is applied. The region where no adhesive material is applied may serve to block a vibration that is generated in and transferred from the periphery. One or a plurality of regions where no adhesive material is applied may be provided.

Through the above-described process, the respiratory sensing device 1000 may sense a vibration due to respiration while minimizing noise.

Figure 12:
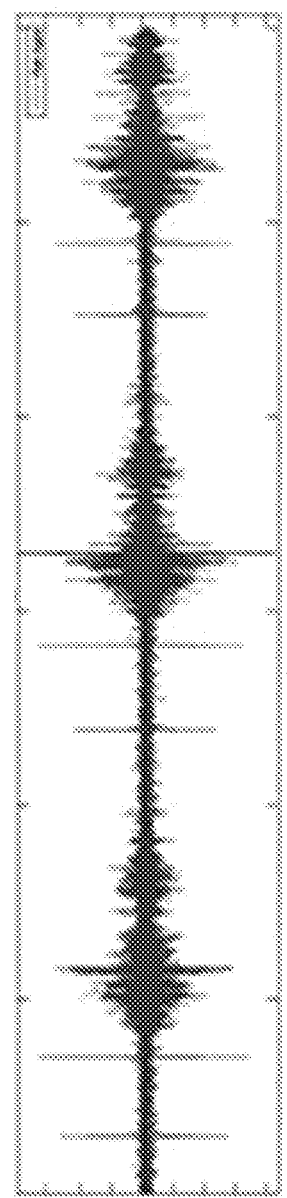
FIG. 12 shows a respiratory signal sensed in FIG. 11.
Figure 13:
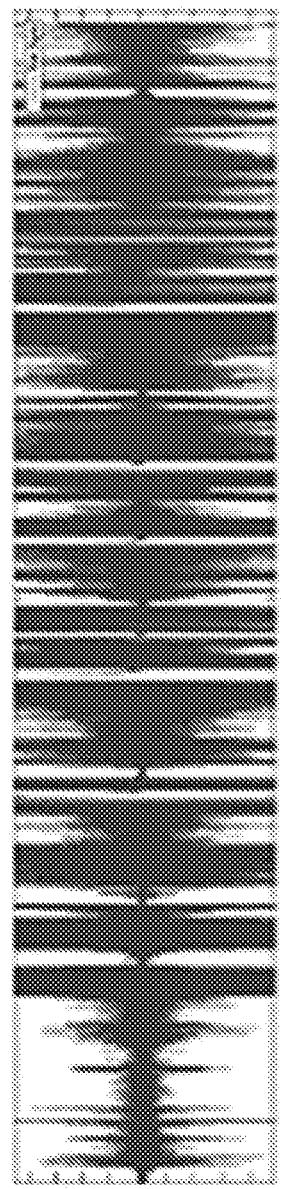
FIG. 13 shows an example of a respiratory signal sensed by a respiratory sensing device omitting an insulating film.

FIG. 12 shows a respiratory signal sensed through the respiratory sensing device 1000 in FIG. 11, and FIG. 13 shows a respiratory signal sensed by the respiratory sensing device 1000 omitting the insulating film 1440.

Referring to FIG. 12, it can be seen that a vibration due to respiration appears as electric signal waveforms.

A large amplitude of the electric signal refers to the occurrence of a movement due to respiration. It can be seen that the electric signal is generated at a certain frequency and also amplitude. This indicates that respiration occurs at regular intervals and is maintained in a normal state without any sudden change in movement.

When viewing the waveforms of the electric signal, it can be seen that a difference between an amplitude when there is a movement and an amplitude when there is no movement is very distinct. Such a high-quality signal may be seen as reduced noise due to the piezoelectric film 1460 being well insulated from a human body and an external element by the insulating film 1440 and due to the piezoelectric film 1460 being grounded to a human body part.

Referring to FIG. 13, it can be seen that an electric signal is large in amplitude and an electric signal has so much noise that a vibration due to respiration cannot be checked, that is, an electric signal is sensed from many frequency bands irrespective of respiration.

This is because the lower electrode 1480b of the piezoelectric film 1460 is in contact with the human body in all regions without being electrically disconnected by the insulating film 1440. In this case, even small body surface currents such as ECG and EMG may act as noise for electrical signals generated through the piezoelectric effect.

Figure 14:
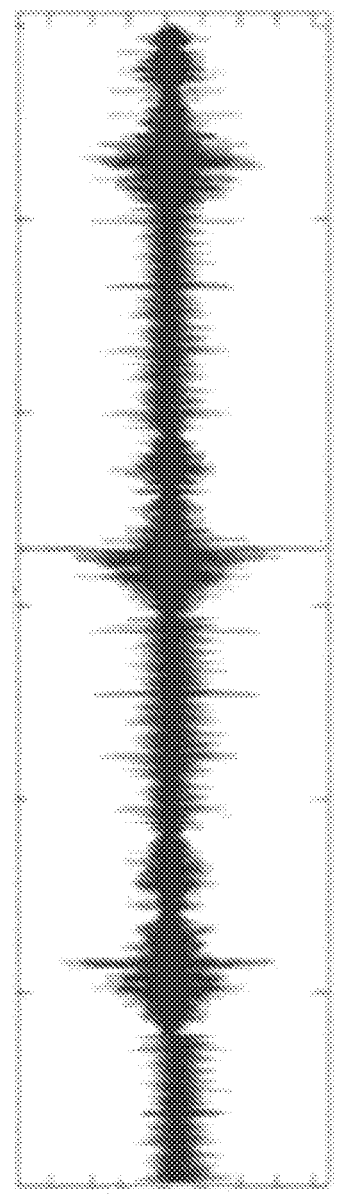
FIG. 14 shows an example of a respiratory signal sensed by a respiratory sensing device with a lower electrode not being grounded.

FIG. 14 shows a respiratory signal sensed by the respiratory sensing device 1000 with a lower electrode not being grounded.

As shown, when grounding is not performed, a vibration due to exhalation may be distinct from a vibration due to inhalation, but a signal amplitude difference is not distinct. This may result in very poor signal quality.

Generally, the grounding of an electronic product may largely influence the performance. Through grounding, an electronic product may perform noise filtering, thus improving life expectancy.

Since the human body has a relatively huge electric capacity compared to the respiratory sensing device 1000, it is possible to grant electrical stability to the respiratory sensing device 1000. In particular, since the electrical signal generated by the respiratory sensing device 1000 is small in size and sensitive to noise, the role of the grounding which may grant electrical stability is even greater by setting a reference potential.

Figure 23:
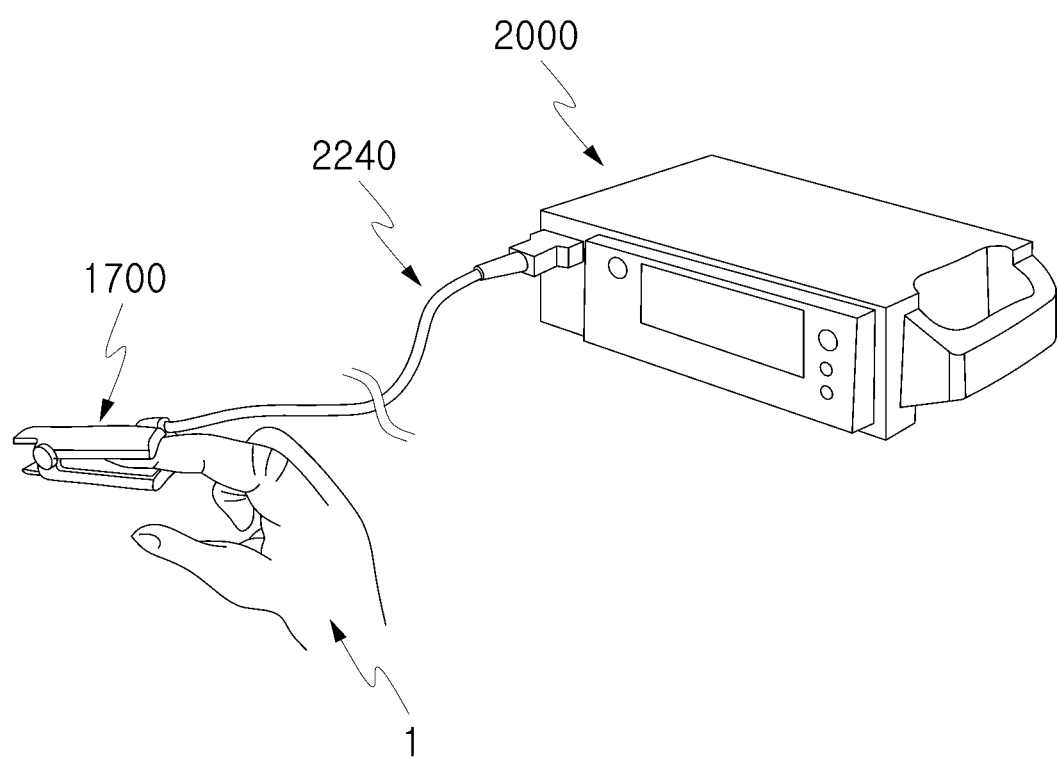
FIG. 23 is a diagram showing a usage state of a pulse oximeter according to an embodiment of the present invention.
Figure 24:
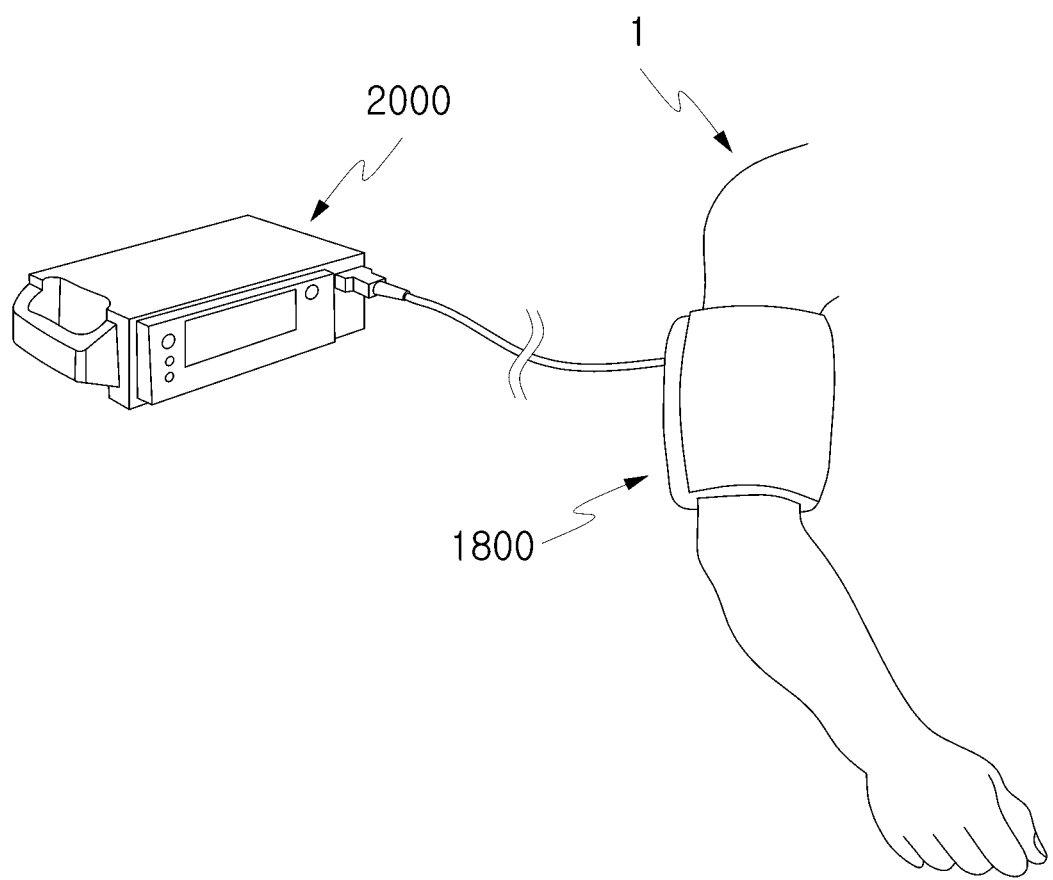
FIG. 24 is a diagram showing a usage state of an upper arm blood pressure monitor according to an embodiment of the present invention.
Figure 25:
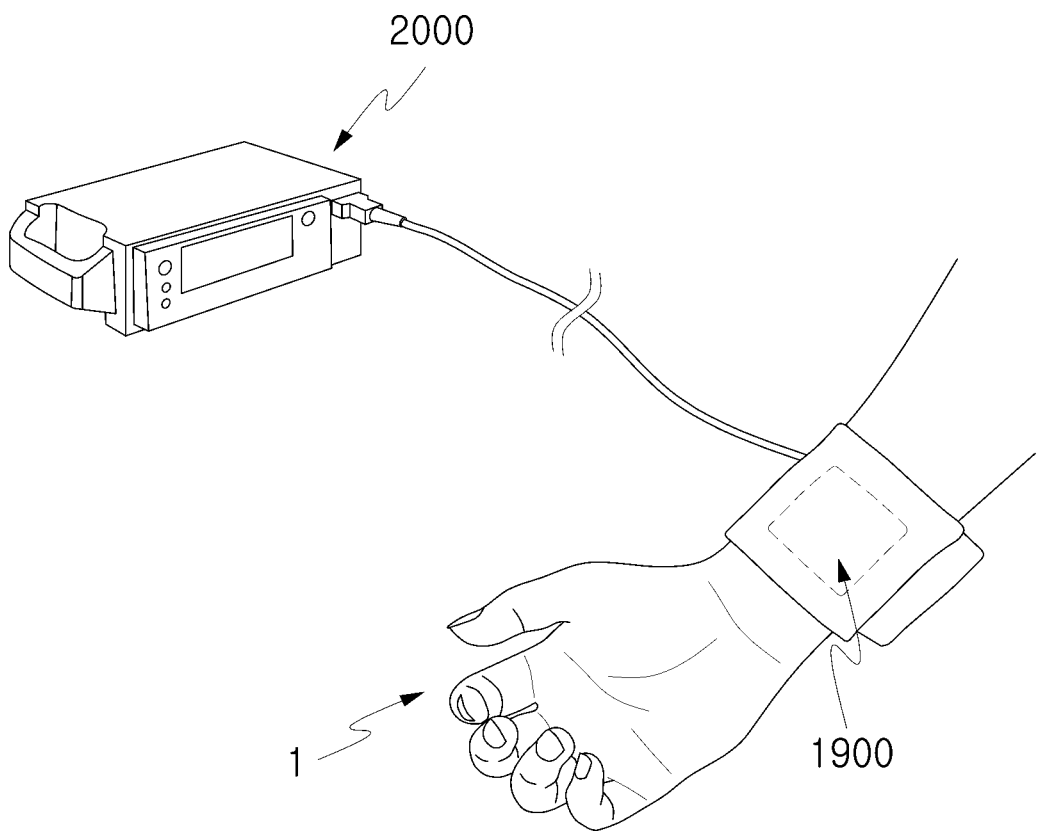
FIG. 25 is a diagram showing a usage state of a wrist blood pressure monitor according to an embodiment of the present invention.
Figure 26:
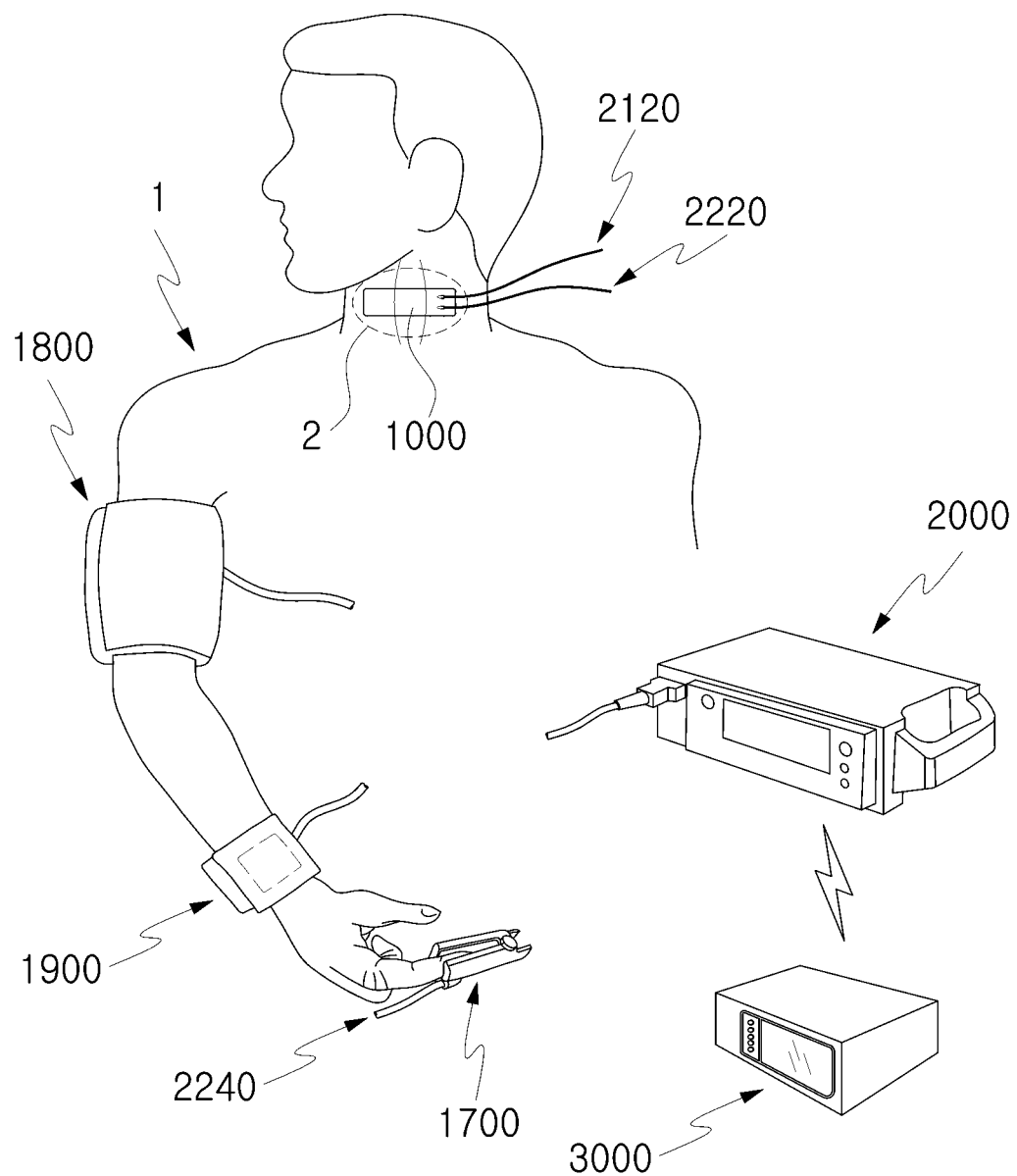
FIG. 26 is still another schematic diagram of a respiratory monitoring system according to an embodiment of the present invention.

FIG. 23 is a diagram showing a usage state of a pulse oximeter according to an embodiment of the present invention, FIG. 24 is a diagram showing a usage state of an upper arm blood pressure monitor according to an embodiment of the present invention, FIG. 25 is a diagram showing a usage state of a wrist blood pressure monitor according to an embodiment of the present invention, and FIG. 26 is still another schematic diagram of a respiratory monitoring system according to an embodiment of the present invention.

Referring to FIGS. 23 to 25, an interface device 2000 may be connected to a respiratory sensing device 1000 and also to other types of apparatuses.

Referring to FIG. 23, the interface device 2000 may be electrically connected to a pulse oximeter 1700 that measures blood oxygen saturation. The pulse oximeter 1700 is an apparatus for directing light of two different wavelengths from a semiconductor device to one point of a finger and non-invasively measuring blood oxygen saturation.

In this case, the interface device 2000 may receive a signal including oxygen saturation information generated from the pulse oximeter through the second communication cable 2240.

The pulse oximeter 1700 may include a separate battery. Also, a separate battery may not be included in the pulse oximeter 1700. In this case, the interface device 2000 may supply power to the pulse oximeter 1700 through the second power cable 2140.

The interface device 2000 may generate a respiratory signal in further consideration of the oxygen saturation information measured through the pulse oximeter 1700. In this case, the respiratory sensing device 1000 may measure a signal occurring immediately upon respiration, and the pulse oximeter 1700 may measure blood oxygen saturation. Thus, the interface device 2000 may generate a respiratory signal using a temporal difference between the measurements. In more detail, a change in blood oxygen saturation occurs only after a respiratory disorder occurs such that the change may respond more slowly than the respiratory signal measured by the respiratory sensing device 1000. Accordingly, the interface device 2000 may process a piezoelectric signal generated by the respiratory sensing device 1000. When the change in blood oxygen saturation is found by the pulse oximeter 1700, the interface device 2000 may reflect the change in the respiratory signal prior to the piezoelectric signal.

An upper arm blood pressure monitor 1950 is an apparatus that is attached to an upper arm of the patient 1 to measure blood pressure. The interface device 2000 may be electrically connected to the upper arm blood pressure monitor 1950 to receive a signal including upper arm blood pressure information. In this case, the interface device 2000 may be wired to the upper arm blood pressure monitor 1950 by cable.

Also, the upper arm blood pressure monitor 1950 may receive separate power from the outside and may receive power from the battery 2100 of the interface device 2000. It will be appreciated that a separate battery is installed in the upper arm blood pressure monitor 1950 to supply power.

The interface device 2000 may be installed in the upper arm blood pressure monitor. In this case, the controller 2200 of the interface device 2000 may receive a signal including upper arm blood pressure information from the upper arm blood pressure monitor 1950.

A wrist blood pressure monitor 1900 is an apparatus that senses Korotkoff sounds from the wrist of the patient 1 and measures blood pressure corresponding to a wrist blood pressure value. In this case, the wrist blood pressure monitor 1900 may use a piezo sensor in the form of an array sensor to accurately place a sensor for detecting Korotkoff sounds at a radial artery. That is, since the piezo sensor is implemented as an array sensor, it is possible to improve the fit-feeling of the wrist blood pressure monitor and also to accurately measure blood pressure even when the blood pressure monitor is partially deviated or misaligned.

The wrist blood pressure monitor 1900 may correct the blood pressure corresponding to the wrist blood pressure value in the radial artery of the wrist into a signal reflecting an upper arm blood pressure value.

The interface device 2000 may be electrically connected to the wrist blood pressure monitor 1900 to receive a signal reflecting the upper arm blood pressure value. In this case, the interface device 2000 may be wired to the wrist blood pressure monitor 1900 by cable. Also, the wrist blood pressure monitor 1900 may receive separate power and receive power from the battery 2100 of the interface device 2000.

FIG. 26 is another schematic diagram of the respiratory monitoring system according to an embodiment of the present invention.

Referring to FIG. 26, the interface device 2000 may be electrically connected to at least one of the respiratory sensing device 1000, the pulse oximeter 1700, the upper arm blood pressure monitor 1950, and the wrist blood pressure monitor 1900.

As described above, the interface device 2000 may receive a piezoelectric signal from the respiratory sensing device 1000. The interface device 2000 may receive a signal including blood oxygen saturation information from the pulse oximeter 1700. The interface device 2000 may receive a signal including upper arm blood pressure information from the upper arm blood pressure monitor 1950. Also, the interface device 2000 may receive a signal reflecting an upper arm blood pressure value from the wrist blood pressure monitor 1900.

The interface device 2000 may transmit, to the respiratory monitoring device 3000, a respiratory signal reflecting the piezoelectric signal and the signal including the oxygen saturation information. Also, the interface device 2000 may transmit, to the respiratory monitoring device 3000, a blood pressure signal reflecting the signal reflecting the upper arm blood pressure value and the signal including the upper arm blood pressure information. In this case, the respiratory monitoring device 3000 may display the blood pressure signal in addition to the respiratory signal.

As described above, the respiratory sensing device 1000 and the respiratory monitoring device 3000 including the same according to an embodiment of the present invention may measure a vibration due to respiration of a patient 1 using the piezoelectric effect to acquire an electrical signal with minimized noise, acquire a respiratory state of the patient 1 on the basis of the acquired electrical signal, and provide the respiratory state to a user.

While the elements and features of the present invention have been described with reference to embodiments of the present invention, the present invention is not limited thereto. It will be obvious to those skilled in the art that various changes or modifications may be made therein without departing from the spirit and scope of the present invention. Accordingly, such changes or modifications are intended to fall within the scope of the appended claims.

MODE OF THE INVENTION

Various embodiments have been described in the best mode for carrying out the invention.

INDUSTRIAL APPLICABILITY

As described above, the present invention can be wholly or partially applied to the respiratory sensing device and the respiratory monitoring system including the same.

The invention claimed is:

1. A respiratory sensing device configured to sense a vibration generated due to a patient's respiration using a piezoelectric effect comprising:
   a piezoelectric film including a thin film-shaped piezoelectric material, an upper electrode placed over the piezoelectric material, and a lower electrode placed under the piezoelectric material, wherein the piezoelectric material is interposed between the upper electrode and the lower electrode, and the piezoelectric film is configured to generate an electrical signal to the upper electrode and the lower electrode according to the vibration generated due to the patient's respiration;
   an adhesive layer laced under the piezoelectric film to face the lower electrode, wherein the adhesive layer includes an adhesive material for being attached to the patient's body, and the adhesive layer is configured to transfer the vibration generated due to the patient's respiration to the piezoelectric film, the adhesive layer having an upper surface and a lower surface electrically connected to each other due to conductivity, wherein the adhesive layer is made of a hydrogel; and
an insulating film interposed between the piezoelectric film and the adhesive layer and configured to block an electrical connection between the piezoelectric film and the adhesive layer,
wherein a through-hole is formed in the insulating film, and the lower electrode is capable of being grounded by at least part of the lower electrode, through the through-hole, electrically connected with the insulating film for being attached to the patient's body so that a noise of the electrical signal due to the piezoelectric effect decreases; and
wherein the lower electrode is grounded to the patient's body by a portion of the hydrogel being inserted into the through-hole and brought into contact with a lower surface of the lower electrode.

2. The respiratory sensing device of claim 1, wherein the through-hole is an empty space extending to pass from an upper surface of the insulating film to a lower surface of the insulating film.

3. The respiratory sensing device of claim 1, wherein,
the piezoelectric film comprises a sensing region for generating an electrical signal according to a vibration by overlapping and stacking the upper electrode, the piezoelectric material, and the lower electrode in the same region when viewed from a direction perpendicular to the piezoelectric film,
each of the upper electrode and the lower electrode has an opposing part placed in the sensing region and a terminal part extending to protrude outward from the opposing part in order to transmit the electrical signal to an outside region, and
the through-hole is formed at a position of the insulating film corresponding to the opposing part of the lower electrode.

4. A respiratory monitoring system configured to output information regarding a patient's respiratory condition acquired by sensing a vibration generated due to the patient's respiration using a piezoelectric effect, the respiratory monitoring system comprising:
a respiratory sensing device comprising:
a piezoelectric film including a thin film-shaped piezoelectric material, an upper electrode placed over the piezoelectric material, and a lower electrode placed under the piezoelectric material, wherein the upper electrode and the lower electrode face each other with the piezoelectric material interposed there between, and the piezoelectric film is configured to generate an electrical signal to the upper electrode and the lower electrode according to the vibration generated due to the patient's respiration;
an adhesive layer placed under the piezoelectric film to face the lower electrode, wherein the adhesive layer includes an adhesive material for being attached to the patient's body, and the adhesive layer is configured to transfer the vibration generated due to the patient's respiration to the piezoelectric film, the adhesive layer having an upper surface and a lower surface electrically connected to each other due to conductivity, wherein the adhesive layer is made of a hydrogel; and
an insulating film interposed between the piezoelectric film and the adhesive layer and configured to block an electrical connection between the piezoelectric film and the adhesive layer, wherein a through-hole is formed in the insulating film wherein the lower electrode is capable of being grounded by at least part of the lower electrode, through the through-hole, electrically connected with the insulating film for being attached to the patient's body through the adhesive layer in order to decrease noise of the electrical signal due to the piezoelectric effect; and
a respiratory monitoring device configured to receive the electrical signal from the respiratory sensing device and output the information regarding the patient's respiratory condition on the basis of the electrical signal,
wherein the lower electrode is grounded to the patient's body by a portion of the hydrogel being inserted into the through-hole and brought into contact with a lower surface of the lower electrode.

5. A respiratory monitoring system configured to display information regarding a patient's respiratory state acquired by sensing a vibration generated due to the patient's respiration using a piezoelectric effect, the respiratory monitoring system comprising:
a disposable respiratory sensing device comprising:
a piezoelectric film including a thin film-shaped piezoelectric material, an upper electrode placed over the piezoelectric material, and a lower electrode placed under the piezoelectric material wherein the piezoelectric material is interposed between the upper electrode and the lower electrode, wherein the piezoelectric film is configured to generate a piezoelectric signal to the upper electrode and the lower electrode according to the vibration generated due to the patient's respiration; and
an adhesive layer placed under the piezoelectric film to face the lower electrode, wherein the adhesive layer includes an adhesive material for being attached to the patient's body, and the adhesive layer is configured to transfer the vibration generated due to the patient's respiration to the piezoelectric film, the adhesive layer having an upper surface and a lower surface electrically connected to each other due to conductivity; and
an insulating film placed under the lower electrode and configured to block an electrical connection from the piezoelectric film;
wherein a through-hole is formed in the insulating film, wherein the lower electrode is capable of being grounded by at least part of the lower electrode, through the through-hole, electrically connected with the insulating film for being attached to the patient's body, so that a noise of the electrical signal due to the piezoelectric effect decreases; and
an interface device comprising:
a battery;
a first power cable configured to supply power to the disposable respiratory sensing device from the battery;
a first communication cable configured to receive the piezoelectric signal from the disposable respiratory sensing device;
a controller configured to process the piezoelectric signal received through the first communication cable to generate a respiratory signal; and
a communication module configured to transmit the respiratory signal to an external device, wherein:
the interface device determines that a patient's airway (trachea) is not secured when the piezoelectric signal corresponds to a first predetermined condition and determines that a patient is in a sleep apnea state when the piezoelectric signal corresponds to a second predetermined condition and then transmits the respiratory signal,
the first predetermined condition is that a time interval at which the piezoelectric signal is sensed by the interface device exceeds a first predetermined time interval or that a number of times the piezoelectric signal is sensed by the interface device per reference time is less than a first predetermined number,
the second predetermined condition is that a time interval at which the piezoelectric signal is sensed by the interface device exceeds a second predetermined time interval or that a number of times the piezoelectric signal is sensed by the interface device per reference time is less than a second predetermined number, and
the second predetermined time interval is greater than the first predetermined time interval, and the second predetermined number is greater than the first predetermined number.

6. The respiratory monitoring system of claim 5, further comprising a respiratory monitoring device configured to receive the respiratory signal from the interface device and display the information regarding the patient's respiratory condition on the basis of the respiratory signal.

7. The respiratory monitoring system of claim 5, further comprising a pulse oximeter installed at one point of a patient's finger and configured to measure blood oxygen saturation,
wherein the interface device comprises a second communication cable having one end electrically connected to the controller and another end electrically connected to the pulse oximeter so that the second communication cable is configured to receive a signal including information regarding the blood oxygen saturation from the pulse oximeter.

8. The respiratory monitoring system of claim 7, wherein the interface device comprises a second power cable for supplying power from the battery to the pulse oximeter.

9. The respiratory monitoring system of claim 7, wherein the interface device generates the respiratory signal in further consideration of the information regarding the oxygen saturation.

10. The respiratory monitoring system of claim 7, further comprising an upper arm blood pressure monitor installed on the patient's upper arm and configured to measure blood pressure of the patient's upper arm,
wherein the interface device is electrically connected to the upper arm blood pressure monitor and configured to receive a signal including the information regarding the blood pressure of the upper arm.

11. The respiratory monitoring system of claim 10, wherein the interface device is installed in the upper arm blood pressure monitor.

12. The respiratory monitoring system of claim 10, further comprising a wrist blood pressure monitor configured to sense Korotkoff sounds from a patient's wrist, measure blood pressure corresponding to a wrist blood pressure value, and correct blood pressure corresponding to the wrist blood pressure value to a signal reflecting an upper arm blood pressure value,
wherein the interface device is electrically connected to the wrist blood pressure monitor and configured to receive the signal reflecting the upper arm blood pressure value.

13. The respiratory monitoring system of claim 5, wherein the communication module is a wireless communication module using at least one of Bluetooth, Zigbee, and Wi-Fi.

14. The respiratory monitoring system of claim 5, wherein,
the interface device determines that the patient is in a snoring state when the piezoelectric signal corresponds to a third predetermined condition and then transmits the respiratory signal, and
the third predetermined condition is that the piezoelectric signal has an amplitude exceeding a predetermined value.

15. The respiratory monitoring system of claim 5, wherein,
the respiratory sensing device comprises an adhesive layer which is placed under the piezoelectric film to face the lower electrode, which is provided as an adhesive material and thus attached to the patient's body, and which is configured to transfer the vibration generated due to the patient's respiration to the piezoelectric film, the adhesive layer having an upper surface and a lower surface electrically connected to each other due to conductivity, and
the insulating film is configured to block an electrical connection between the piezoelectric film and the adhesive layer and has a through-hole formed to electrically connect the lower electrode and the adhesive layer so as to ground the lower electrode to the patient's body through the adhesive layer in order to decrease noise of the electrical signal due to the piezoelectric effect.

* * * * *